US012766329B2

(12) United States Patent
Sakashita et al.

(10) Patent No.: US 12,766,329 B2
(45) Date of Patent: Oct. 20, 2026

(54) DEFIBRILLATION CONTROL DEVICE

(71) Applicant: Japan Lifeline Co., Ltd., Tokyo (JP)

(72) Inventors: Naoya Sakashita, Tokyo (JP); Yasuhiro Kojima, Tokyo (JP)

(73) Assignee: Japan Lifeline Co., Ltd., Tokyo (JP)

( * ) Notice: Subject to any disclaimer, the term of this patent is extended or adjusted under 35 U.S.C. 154(b) by 280 days.

(21) Appl. No.: 18/513,277

(22) Filed: Nov. 17, 2023

(65) Prior Publication Data

US 2024/0285959 A1 Aug. 29, 2024

(30) Foreign Application Priority Data

Feb. 28, 2023 (JP) ................................ 2023-030084

(51) Int. Cl.
*A61N 1/39* (2006.01)
*A61N 1/05* (2006.01)
*A61N 1/372* (2006.01)
*A61N 1/37* (2006.01)

(52) U.S. Cl.
CPC ......... *A61N 1/3925* (2013.01); *A61N 1/0563* (2013.01); *A61N 1/37247* (2013.01); *A61N 1/37258* (2013.01); *A61N 1/3987* (2013.01)

(58) Field of Classification Search
CPC .................... A61N 1/3925; A61N 1/08; A61B 5/321-366; A61B 5/6852-6859
See application file for complete search history.

(56) References Cited

U.S. PATENT DOCUMENTS

| | | | | |
|---|---|---|---|---|
| 4,295,474 A * | 10/1981 | Fischell | ............. A61N 1/37223 | 600/510 |
| 2014/0350621 A1* | 11/2014 | Gunderson | .......... A61N 1/3706 | 607/7 |
| 2023/0181917 A1* | 6/2023 | Sakamoto | ............ A61N 1/0563 | 607/5 |

FOREIGN PATENT DOCUMENTS

| | | | | |
|---|---|---|---|---|
| JP | 4545216 B1 | 9/2010 | | |
| JP | 2013536044 A | 9/2013 | | |
| JP | 2018164737 A | 10/2018 | | |
| JP | 2022539362 A | 9/2022 | | |
| WO | WO-2021251088 A1 * | 12/2021 | ............... A61B 5/33 | |

OTHER PUBLICATIONS

Bhatt, "What happens during electrical cardioversion?", Aug. 1, 2022, Harvard Medical School, Harvard Health Publishing (Year: 2022).*

* cited by examiner

*Primary Examiner* — Unsu Jung
*Assistant Examiner* — Fiona M Kowalkowski
(74) *Attorney, Agent, or Firm* — Shih IP Law Group, PLLC

(57) ABSTRACT

A defibrillation control device includes a power source unit that supplies electrical energy to an electrode catheter, an abnormality detection unit that detects an earliest abnormal waveform by using a plurality of electrocardiographic waveforms measured by a plurality of electrodes of the electrode catheter after supplying the electrical energy, and a warning unit that issues an alert upon detecting the earliest abnormal waveform.

8 Claims, 19 Drawing Sheets

DEFIBRILLATION CONTROL DEVICE

CROSS-REFERENCE TO RELATED APPLICATIONS

This application claims the benefit of priority to Japanese Patent Application Number 2023-030084 filed on Feb. 28, 2023. The entire contents of the above-identified application are hereby incorporated by reference.

TECHNICAL FIELD

The present disclosure relates to a defibrillation control device.

BACKGROUND

Catheter ablation treatment is generally performed by inserting a catheter into a cardiac cavity and locally cauterizing a site considered to be a cause of an arrhythmia. In ablation treatment, a cardiac potential in the cardiac cavity is measured using an electrode catheter inserted into the cardiac cavity, and the site considered to be the cause of the arrhythmia is analyzed. In order to remove atrial fibrillation that may occur during the ablation procedure, an intracardiac defibrillation system is also used to directly supply electrical energy for defibrillation to the heart via the electrode catheter in the cardiac cavity.

Patent Literature

PTL 1: JP 4545216 B

SUMMARY

In the ablation treatment, identifying the site causing the arrhythmia and cauterizing the specified site may be performed simultaneously in parallel. When information useful for diagnosing the site causing the arrhythmia can be provided, the information is beneficial for doctors and the like performing the treatment.

The present disclosure has been made in view of the circumstances described above, and an object thereof is to provide information useful for catheter treatment.

A defibrillation control device of an aspect of the present disclosure includes a power source unit that supplies electrical energy to an electrode catheter, an abnormality detection unit that detects an earliest abnormal waveform by using a plurality of electrocardiographic waveforms measured by a plurality of electrodes of the electrode catheter after supplying the electrical energy, and a warning unit that issues an alert upon detecting the earliest abnormal waveform.

Note that any combinations of the above components and those obtained by converting these expressions into methods, apparatuses, systems, recording media, computer programs, and the like are also included in the present disclosure.

According to the present disclosure, information useful for catheter treatment can be provided.

DESCRIPTION OF EMBODIMENTS

Figure 1:
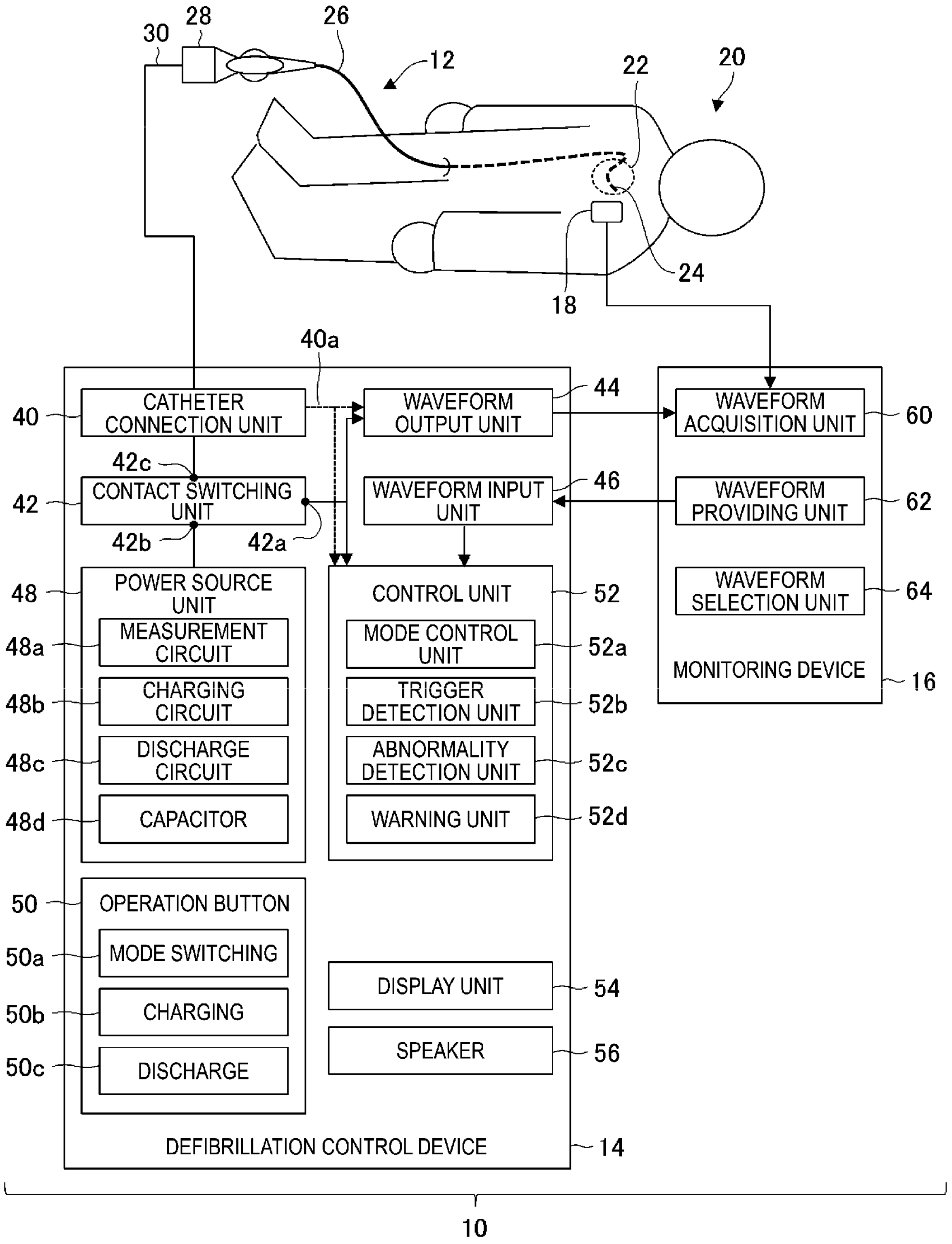
FIG. 1 is a diagram schematically illustrating a configuration of a defibrillation system according to a first embodiment.

Hereinafter, modes for carrying out the present disclosure (hereinafter, also referred to as embodiments) are described in detail with reference to the drawings. In the description and/or drawings, the same or equivalent constituent elements, members, processing operations, and the like are denoted by the same reference numerals, and redundant descriptions are omitted. The scales and shapes of the illustrated parts are set for convenience to simplify the explanation and are not to be construed in a limited manner unless otherwise specified. The embodiments are illustrative and do not limit the scope of the present disclosure in any way. Not all features or combinations of the features described in the embodiments are essential to the present disclosure.

First Embodiment

FIG. 1 is a diagram schematically illustrating a configuration of a defibrillation system 10 according to a first embodiment. The defibrillation system 10 includes an electrode catheter 12, a defibrillation control device 14, and a monitoring device 16.

The electrode catheter 12 is a so-called cardiac catheter. The electrode catheter 12 is inserted into the body of a patient 20 and is used such that a distal end portion 24 of the electrode catheter 12 is positioned in a heart 22 of the patient 20. A plurality of electrodes are provided at a distal end side of the electrode catheter 12 to be arranged in a longitudinal direction. The electrode catheter 12 can measure cardiac potentials at a plurality of locations in a cardiac cavity with the plurality of electrodes. The electrode catheter 12 can directly supply electrical energy for defibrillation to the heart 22 by applying voltages to the plurality of electrodes.

The defibrillation control device 14 is connected to the electrode catheter 12. The defibrillation control device 14 operates in either a cardiac potential measurement mode or a defibrillation mode. In the cardiac potential measurement mode, the defibrillation control device 14 acquires electrocardiographic waveforms measured by the plurality of electrodes of the electrode catheter 12 and outputs the acquired electrocardiographic waveforms to the monitoring device 16. In the defibrillation mode, the defibrillation control device 14 supplies electrical energy for defibrillation to the electrode catheter 12 by applying voltages to the plurality of electrodes of the electrode catheter 12.

The monitoring device 16 acquires and monitors electrocardiographic waveforms of the patient 20. The monitoring device 16 acquires the electrocardiographic waveforms measured by the electrode catheter 12 via the defibrillation control device 14. The monitoring device 16 acquires the electrocardiographic waveforms of the patient 20 via a cardiac potential measurement means such as an electrode pad 18 attached to a body surface of the patient 20. The monitoring device 16 can also acquire the electrocardiographic waveforms of the patient 20 acquired from an electrode catheter different from the electrode catheter 12 connected to the defibrillation control device 14. The monitoring device 16 provides at least one of the acquired electrocardiographic waveforms to the defibrillation control device 14. The electrocardiographic waveform provided from the monitoring device 16 to the defibrillation control device 14 is used to determine a possible supply start timing (trigger point) of the electrical energy for defibrillation.

The defibrillation system 10 is used, for example, in catheter ablation surgery for locally cauterizing a site considered to be a cause of an arrhythmia. During the ablation surgery, atrial fibrillation may occur as a type of arrhythmia. When the atrial fibrillation occurs, electrical energy is supplied via the electrode catheter 12 for defibrillation. When the atrial fibrillation is removed by supplying the electrical energy, a normal heartbeat often begins, but before the normal heartbeat begins, a site being a cause of an arrhythmia may be abnormally excited. In the present embodiment, an earliest abnormal waveform indicating the occurrence of abnormal excitation is detected by analyzing the electrocardiographic waveform after defibrillation. According to the present embodiment, by detecting the earliest abnormal waveform, a doctor or the like can be provided with useful information relating to the cause of the arrhythmia.

Figure 2:
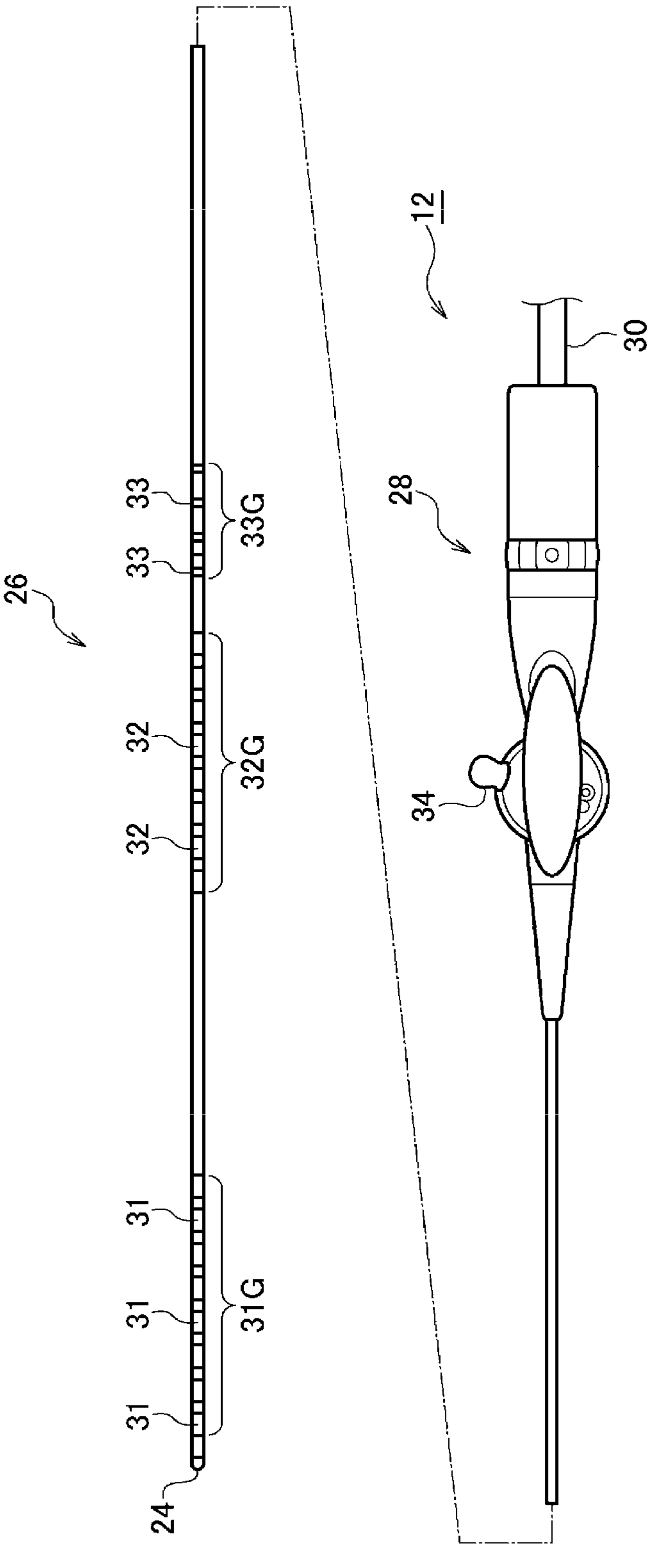
FIG. 2 is a diagram schematically illustrating a structure of an electrode catheter.

FIG. 2 is a diagram schematically illustrating a structure of the electrode catheter 12. The electrode catheter 12 includes a shaft 26 that is flexible, is inserted into the body, and has a tubular shape and a handle portion 28 connected to a proximal end side (outside the body) of the shaft 26. A doctor or the like who is a user of the electrode catheter 12 operates the electrode catheter 12 while gripping the handle portion 28. The user can tilt (swing) the distal end portion 24 of the shaft 26 in a predetermined direction through a pull wire (not illustrated) inserted into the shaft 26 by rotating a knob portion 34 while gripping the handle portion 28. By rotating the handle portion 28 in a circumferential direction, a tilt direction of the distal end portion 24 of the shaft 26 can be adjusted. A cable 30 for connection to the defibrillation control device 14 is connected to an end of the handle portion 28.

A first electrode group 31G, a second electrode group 32G, and a third electrode group 33G are provided on a distal end side of the shaft 26. The positions and order of the first electrode group 31G, the second electrode group 32G, and the third electrode group 33G in an axial direction (longitudinal direction) of the shaft 26 are optional; however, in the example illustrated in FIG. 2, the first electrode group 31G, the second electrode group 32G, and the third electrode group 33G are arranged in this order from the distal end side toward the proximal end side. In performing defibrillation treatment on the inside of the cardiac cavity by the electrode catheter 12 having such an electrode arrangement, for example, the first electrode group 31G on the distal end side is located at a coronary sinus (CS), the second electrode group 32G on the proximal end side is located at a right atrium (RA), and the third electrode group 33G on the further proximal end side is located at a superior vena cava (SVC).

The first electrode group 31G includes a plurality of first electrodes 31 each having a ring shape and being spaced apart from one another in the axial direction. The second electrode group 32G includes a plurality of second electrodes 32 each having a ring shape and being spaced apart from one another in the axial direction. The third electrode group 33G includes a plurality of third electrodes 33 each having a ring shape and being spaced apart from one another in the axial direction. In the example illustrated in FIG. 2, eight first electrodes 31, eight second electrodes 32, and four third electrodes 33 are provided; however, the number of electrodes included in each of the electrode groups 31G, 32G, and 33G is not particularly limited. The plurality of electrodes 31, 32 and 33 need not be collectively arranged for the respective electrode groups 31G, 32G and 33G, and may also be distributedly arranged at any position in the axial direction.

An electrode number may be assigned to each of the plurality of electrodes 31, 32, and 33 provided in the electrode catheter 12. The electrode numbers, for example, are assigned sequentially from the distal end side to the proximal end side of the electrode catheter 12. For example, numbers "1" to "8" are assigned to the eight first electrodes 31 of the first electrode group 31G, numbers "9" to "16" are assigned to the eight second electrodes 32 of the second electrode group 32G, and numbers "17" to "20" are assigned to the four third electrodes 33 of the third electrode group 33G.

A first conducting wire group, a second conducting wire group, and a third conducting wire group (not illustrated) electrically connected to the electrode groups 31G, 32G, and 33G are inserted through the shaft 26. The first conducting wire group includes a plurality of (for example, eight) first conducting wires connected correspondingly to the plurality of first electrodes 31 in the first electrode group 31G. The second conducting wire group includes a plurality of (for example, eight) second conducting wires connected correspondingly to the plurality of second electrodes 32 in the second electrode group 32G. The third conducting wire group includes a plurality of (for example, four) third conducting wires connected correspondingly to the plurality of third electrodes 33 in the third electrode group 33G. Each conducting wire group is electrically connected to the defibrillation control device 14 via the cable 30. In the cardiac potential measurement mode, the defibrillation control device 14 can acquire electrocardiographic waveforms measured by the plurality of electrodes 31, 32, and 33 constituting the electrode groups 31G, 32G, and 33G, respectively.

The electrocardiographic waveform measured using the first electrode group 31G is also referred to as a first electrocardiographic waveform. The first electrocardiographic waveform is, for example, a CS waveform indicating the cardiac potential of the coronary sinus (CS). When the first electrode group 31G includes the eight first electrodes 31, four CS waveforms CS1, CS2, CS3, and CS4 at four locations in the coronary sinus can be measured. Each of the four CS waveforms corresponds to, for example, a temporal change in the potential difference between two adjacent first electrodes 31 in the first electrode group 31G.

The electrocardiographic waveform measured using the second electrode group 32G is also referred to as a second electrocardiographic waveform. The second electrocardiographic waveform is, for example, an RA waveform indicating the cardiac potential of the right atrium (RA). When the second electrode group 32G includes the eight second electrodes 32, four RA waveforms RA1, RA2, RA3, and RA4 at four locations in the right atrium can be measured. Each of the four RA waveforms corresponds to, for example, a temporal change in the potential difference between two adjacent second electrodes 32 in the second electrode group 32G.

The electrocardiographic waveform measured using the third electrode group 33G is also referred to as a third electrocardiographic waveform. The third electrocardiographic waveform is, for example, an SVC waveform indicating the cardiac potential of the superior vena cava (SVC). When the third electrode group 33G includes the four third electrodes 33, SVC waveforms SVC1 and SVC2 at two locations in the superior vena cava can be measured. Each of the two SVC waveforms corresponds to, for example, a temporal change in the potential difference between two adjacent third electrodes 33.

Voltages having different polarities are applied to the first electrode group 31G and the second electrode group 32G by the defibrillation control device 14 in the defibrillation mode. When a positive voltage is applied to the first electrode group 31G, a negative voltage is applied to the second electrode group 32G. For example, a common positive voltage is applied to the plurality of first electrodes 31 constituting the first electrode group 31G, and a common negative voltage is applied to the plurality of second electrodes 32 constituting the second electrode group 32G. Conversely, when a negative voltage is applied to the first electrode group 31G, a positive voltage is applied to the second electrode group 32G. For example, a common negative voltage is applied to the plurality of first electrodes 31 constituting the first electrode group 31G, and a common positive voltage is applied to the plurality of second electrodes 32 constituting the second electrode group 32G. In this manner, electrical energy for defibrillation can be directly supplied between the coronary sinus CS disposed with the first electrode group 31G and the right atrium RA disposed with the second electrode group 32G.

Referring back to FIG. 1, the defibrillation control device 14 is described. The defibrillation control device 14 includes a catheter connection unit 40, a contact switching unit 42, a waveform output unit 44, a waveform input unit 46, a power source unit 48, an operation button 50, a control unit 52, a display unit 54, and a speaker 56.

The cable 30 connected to the electrode catheter 12 is attached to the catheter connection unit 40. The catheter connection unit 40 includes a connection terminal group electrically connected to each of the plurality of electrodes 31, 32, and 33 respectively constituting the electrode groups 31G, 32G, and 33G of the electrode catheter 12. The catheter connection unit 40 includes a first connection terminal group electrically connected to the first electrode group 31G, a second connection terminal group electrically connected to the second electrode group 32G, and a third connection terminal group electrically connected to the third electrode group 33G. The first connection terminal group and the second connection terminal group are connected to the contact switching unit 42. As indicated by a broken line 40*a*, the third connection terminal group is connected not to the contact switching unit 42 but to the waveform output unit 44 and the control unit 52.

The contact switching unit 42 is a one-circuit-two-contact switching switch, and is configured to connect a common contact 42*c* to either a first contact 42*a* or a second contact 42*b*.

The first connection terminal group and the second connection terminal group of the catheter connection unit 40 are connected to the common contact 42*c*. Consequently, the common contact 42*c* is connected to the first electrode group 31G and the second electrode group 32G of the electrode catheter 12. The first contact 42*a* is connected to the waveform output unit 44 and the control unit 52. The second contact 42*b* is electrically connected to the power source unit 48.

For example, in the cardiac potential measurement mode, the contact switching unit 42 connects the common contact 42*c* to the first contact 42*a*. By connecting the common contact 42*c* to the first node 42*a*, the first electrocardiographic waveform measured by the first electrode group 31G and the second electrocardiographic waveform measured by the second electrode group 32G can be output to the monitoring device 16 via the waveform output unit 44. By connecting the common contact 42*c* to the first node 42*a*, the first electrocardiographic waveform and the second electrocardiographic waveform can be analyzed by the control unit 52. For example, in the defibrillation mode, the contact switching unit 42 connects the common contact 42*c* to the second contact 42*b*. By connecting the common contact 42*c* to the second contact 42*b*, the first electrode group 31G and the second electrode group 32G are connected to the power source unit 48 so that electrical energy can be supplied from the power source unit 48.

The waveform output unit 44 outputs the electrocardiographic waveforms measured using the electrode catheter 12 toward the monitoring device 16. The waveform output unit 44 includes, for example, a first output terminal group that outputs a plurality of first electrocardiographic waveforms measured by the first electrode group 31G, a second output terminal group that outputs a plurality of second electrocardiographic waveforms measured by the second electrode group 32G, and a third output terminal group that outputs a plurality of third electrocardiographic waveforms measured by the third electrode group 33G.

For example, in the cardiac potential measurement mode, the waveform output unit 44 outputs the first electrocardiographic waveform and the second electrocardiographic waveform. The first electrocardiographic waveform and the second electrocardiographic waveform output from the waveform output unit 44 pass through the contact switching unit 42. For example, when the first contact 42*a* is disconnected from the common contact 42*c* in the defibrillation mode, the waveform output unit 44 does not output the first electrocardiographic waveform and the second electrocardiographic waveform. In both the cardiac potential measurement mode and the defibrillation mode, the waveform output unit 44 outputs the third electrocardiographic waveform. This is because the third electrocardiographic waveform output from the waveform output unit 44 does not pass through the contact switching unit 42.

The electrocardiographic waveform provided from the monitoring device 16 is input to the waveform input unit 46. The waveform input unit 46 includes, for example, an input terminal for receiving the electrocardiographic waveform provided from the monitoring device 16. The electrocardiographic waveform input to the waveform input unit 46 is, for example, a body surface electrocardiographic waveform measured by the electrode pad 18. The electrocardiographic waveform input to the waveform input unit 46 may be an intracardiac electrocardiographic waveform measured by another electrode catheter different from the electrode catheter 12. The electrocardiographic waveform input to the waveform input unit 46 may be the third electrocardiographic waveform measured by the third electrode group 33G of the electrode catheter 12.

The power source unit 48 is connected to the second contact 42*b* of the contact switching unit 42. The power source unit 48 is connected to the catheter connection unit 40 in the defibrillation mode, and is disconnected from the catheter connection unit 40 in the cardiac potential measurement mode. The power source unit 48 is connected to the first electrode group 31G and the second electrode group 32G of the electrode catheter 12 in the defibrillation mode, and is disconnected from the first electrode group 31G and the second electrode group 32G of the electrode catheter 12 in the cardiac potential measurement mode.

In the defibrillation mode, the power source unit 48 supplies electrical energy necessary for defibrillation treatment to the electrode catheter 12. The power source unit 48 includes a measurement circuit 48*a*, a charging circuit 48*b*, a discharge circuit 48*c*, and a capacitor 48*d*.

The measurement circuit 48*a* measures an impedance between the first electrode group 31G and the second electrode group 32G. The impedance measured by the measurement circuit 48*a* is used to determine whether the first electrode group 31G and the second electrode group 32G are appropriately in contact with a tissue in the cardiac cavity and are in a state suitable for supplying the electrical energy for defibrillation. For example, when the impedance measured by the measurement circuit 48*a* is 21 Ω or more and 99 Ω or less, the state is determined to be appropriate for defibrillation.

The charging circuit 48*b* charges the capacitor 48*d* with the electrical energy for defibrillation. The charging circuit 48*b* is configured by, for example, a booster circuit that generates a high voltage of about 100 V to about 600 V. The amount of energy charged in the capacitor 48*d* by the charging circuit 48*b* is configured to be variable by an input operation from a user.

The discharge circuit 48*c* supplies the electrical energy charged in the capacitor 48*d* to the first electrode group 31G and the second electrode group 32G of the electrode catheter 12. The discharge circuit 48*c* is configured by, for example, an H-bridge circuit using four switch elements (for example, transistors). By switching the four switch elements on and off, the discharge circuit 48*c* generates a first state in which a positive voltage is applied to the first electrode group 31G and a negative voltage is applied to the second electrode group 32G, and a second state in which a negative voltage is applied to the first electrode group 31G and a positive voltage is applied to the second electrode group 32G.

Figure 3:
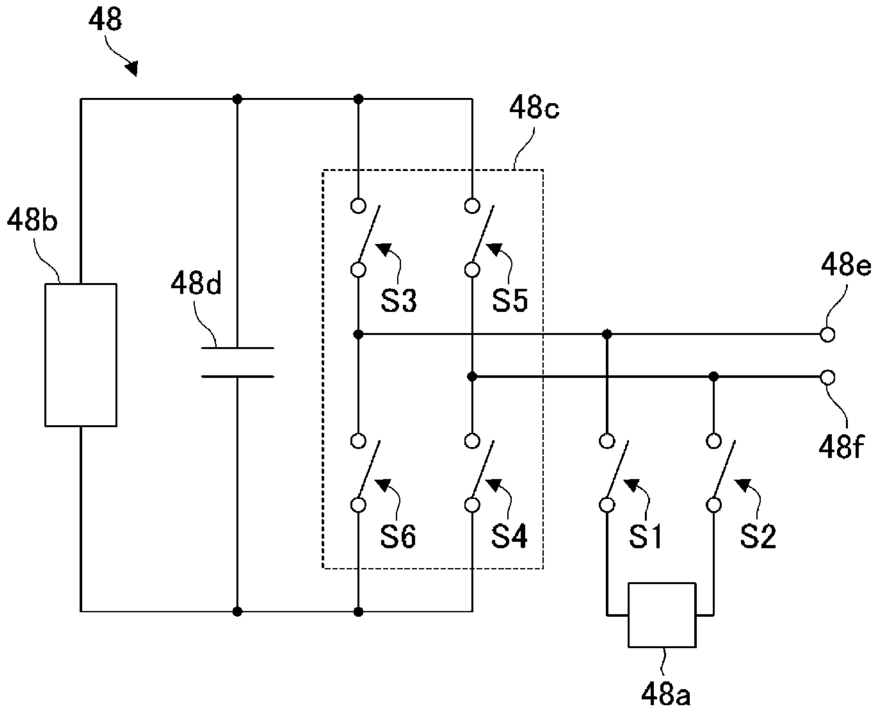
FIG. 3 is a diagram schematically illustrating a circuit configuration of a power source unit.

FIG. 3 is a diagram schematically illustrating a circuit configuration of the power source unit 48. The power source unit 48 includes a first terminal 48*e* connectable to the first electrode group 31G and a second terminal 48*f* connectable to the second electrode group 32G. The measurement circuit 48*a* is connected to the first terminal 48*e* and the second terminal 48*f* via a first switch S1 and a second switch S2. The discharge circuit 48*c* includes a third switch S3, a fourth switch S4, a fifth switch S5, and a sixth switch S6 constituting the H-bridge.

When an impedance between the first terminal 48*e* and the second terminal 48*f* is measured by the measurement circuit 48*a*, the first switch S1 and the second switch S2 are turned on, and the four switches S3 to S6 of the discharge circuit 48*c* are turned off. When the capacitor 48*d* is charged by the charging circuit 48*b*, all the switches S1 to S6 are turned off. Discharge of the capacitor 48*d* by the discharge circuit 48*c* enables the use of a first state in which the third switch S3 and the fourth switch S4 are turned on and the fifth switch S5 and the sixth switch S6 are turned off, and a second state in which the third switch S3 and the fourth switch S4 are turned off and the fifth switch S5 and the sixth switch S6 are turned on.

Figure 4:
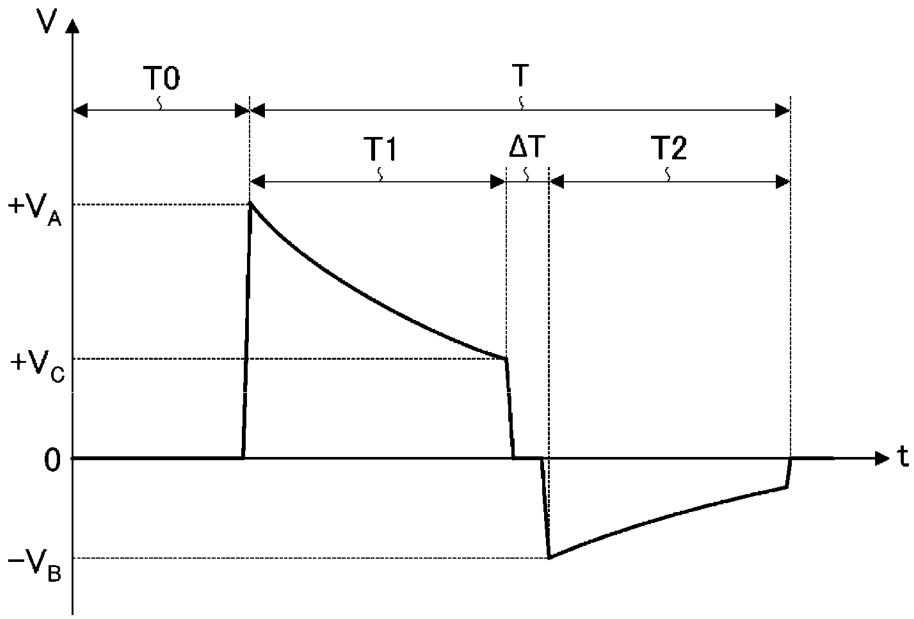
FIG. 4 is a graph showing an example of a voltage waveform output from the power source unit.

FIG. 4 is a graph illustrating an example of a voltage waveform output from the power source unit 48, and illustrates a temporal change in a voltage applied between the first electrode group 31G and the second electrode group 32G. First, voltage application is started after a waiting period T0 elapses from a defibrillation start timing (trigger point). The waiting period T0 is, for example, about 10 to about 50 ms (milliseconds), and is, for example, 10 ms. A first period T1 is a first state in which a positive voltage is applied to the first terminal 48*e* and a negative voltage is applied to the second terminal 48*f*. In the first period T1, the magnitude of the applied voltage decreases from a first peak voltage $V_A$ over time. The magnitude of the first peak voltage $V_A$ corresponds to the charging voltage of the capacitor 48*d* and is about 100 V to about 600 V. A second period T2 is a second state in which a negative voltage is applied to the first terminal 48*e* and a positive voltage is applied to the second terminal 48*f*. In the second period T2, the magnitude of the applied voltage decreases from a second peak voltage $V_B$ over time. The magnitude of the second peak voltage $V_B$ is substantially the same as the magnitude of a voltage $V_C$ at the end of the first period T1. An interval period ΔT between the first period T1 and the second period T2 is a short time required for switching the switches S3 to S6 of the discharge circuit 48*c* on and off. A discharge period T including the first period T1 and the second period T2 is, for example, about 6 ms to about 30 ms, and is, for example, 20 ms.

Referring back to FIG. 1, the operation button 50 is a switch such as a push button for receiving an input operation by a user. The operation button 50 includes a mode switching button 50*a*, a charging button 50*b*, and a discharge button 50*c*. The mode switching button 50*a* is used to switch an operation mode between the cardiac potential measurement mode and the defibrillation mode. The charging button 50*b* is used to start charging the capacitor 48*d* by the charging circuit 48*b* in the defibrillation mode. The discharge button 50*c* is used to start discharging from the capacitor 48*d* by the discharge circuit 48*c* in the defibrillation mode.

The control unit 52 controls the overall operation of the defibrillation control device 14. The control unit 52 includes a mode control unit 52*a*, a trigger detection unit 52*b*, an abnormality detection unit 52*c*, and a warning unit 52*d*.

The mode control unit 52*a* switches the operation mode of the defibrillation control device 14 according to the operation of the operation button 50 by the user. The trigger detection unit 52*b* detects a trigger point at which discharge for defibrillation starts, based on the electrocardiographic waveform provided from the monitoring device 16. The abnormality detection unit 52*c* analyzes the electrocardiographic waveform after completion of the discharge for defibrillation and detects an abnormality in the electrocardiographic waveform. When an event to be alerted to the user occurs, the warning unit 52*d* issues an alert by a warning display by the display unit 54 or a warning sound by the speaker 56.

Figure 5:
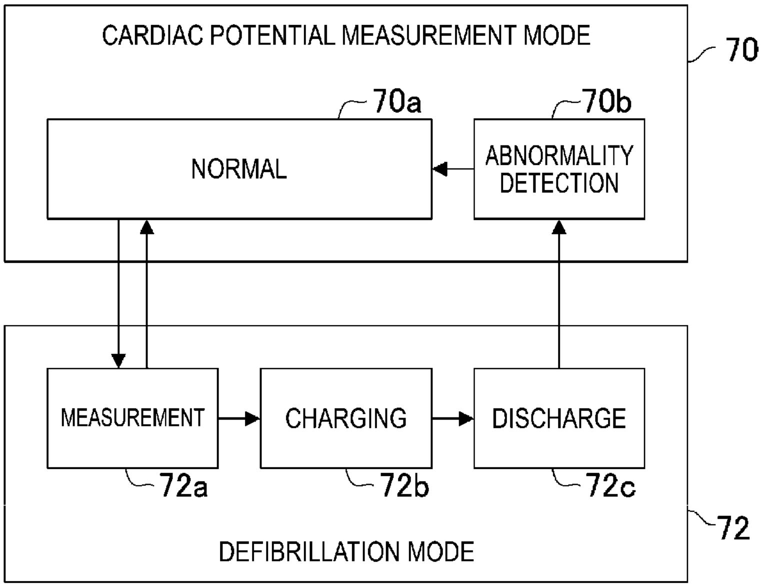
FIG. 5 is a diagram schematically illustrating a transition of an operation mode of a defibrillation control device.

FIG. 5 is a diagram schematically illustrating a transition of the operation mode of the defibrillation control device 14. As described above, the defibrillation control device 14 includes a cardiac potential measurement mode 70 and a defibrillation mode 72 as operation modes. The cardiac potential measurement mode 70 includes a normal mode 70*a* and an abnormality detection mode 70*b*. The defibrillation mode 72 includes a measurement mode 72*a*, a charging mode 72*b*, and a discharge mode 72*c*.

When the mode switching button 52*a* is pressed in the normal mode 70*a*, the mode control unit 50*a* switches an operation mode to the defibrillation mode 72 and shifts to the measurement mode 72*a*. In the measurement mode 72*a*, the impedance between the first electrode group 31G and the second electrode group 32G is measured by the measurement circuit 48*a*. When shifting to the measurement mode 72*a*, the mode control unit 52*a* switches contacts of the contact switching unit 42 and connects the common contact 42*c* to the second contact 42*b*. When the impedance measurement by the measurement circuit 48*a* is completed, the mode control unit 52*a* switches the contacts of the contact switching unit 42 and returns the common contact 42*c* to the first contact 42*a*. When a value of the measured impedance is within a predetermined range (for example, 21 Ω or more and 99 Ω or less), the mode control unit 52*a* shifts to the charging mode 72*b*. When the measured impedance value is out of the predetermined range, the mode control unit 52*a* shifts to the normal mode 70*a*. When the value of the measured impedance is out of the predetermined range, for example, the position of the electrode catheter 12 in the cardiac cavity is adjusted by the user so that the first electrode group 31G and the second electrode group 32G appropriately come into contact with the tissue in the cardiac cavity.

In the charging mode 72*b*, the capacitor 48*d* is charged by the charging circuit 48*b*. When the charging button 50*b* is pressed in the charging mode 72*b*, the mode control unit 52*a* causes the charging circuit 48*b* to start charging the capacitor 48*d*. When the charging button 50*b* is not pressed in the charging mode 72*b*, the mode control unit 52*a* does not cause the charging circuit 48*b* to start charging the capacitor 48*d*. The mode control unit 52*a* does not switch the contacts of the contact switching unit 42 in the charging mode 72*b*, and the common contact 42*c* remain connected to the first contact 42*a*. When charging of the capacitor 48*d* is completed, the mode control unit 52*a* shifts to the discharge mode 72*c*.

In the discharge mode 72*c*, the discharge circuit 48*c* discharges electricity from the capacitor 48*d* to the electrode catheter 12. When the discharge button 50*c* is pressed in the discharge mode 72*c*, the mode control unit 52*a* enters a state of waiting for detection of a trigger point by the trigger detection unit 52*b*. Subsequently, when the trigger point is detected by the trigger detection unit 52*b*, the mode control unit 52*a* switches the contacts of the contact switching unit 42, connects the common contact 42*c* to the second contact 42*b*, and then operates the discharge circuit 48*c* to supply electrical energy to the electrode catheter 12. After discharge by the discharge circuit 48*c* is completed, the mode control unit 52*a* switches the contacts of the contact switching unit 42, returns the common contact 42*c* to the first contact 42*a*, and shifts to the abnormality detection mode 70*b*.

In the abnormality detection mode 70*b*, the presence or absence of a waveform abnormality is detected based on the electrocardiographic waveform measured by the electrode catheter 12. In the abnormality detection mode 70*b*, the abnormality detection unit 52*c* detects the presence or absence of an earliest abnormal waveform and cardiac arrest. The warning unit 52*d* alerts the user when the earliest abnormal waveform or cardiac arrest is detected. When a predetermined button operation for stopping the alert is performed by the user, the mode control unit 52*a* shifts to the normal mode 70*a*. When the earliest abnormal waveform or cardiac arrest is not detected, the mode control unit 52*a* shifts to the normal mode 70*a*.

The trigger detection unit 52*b* detects a trigger point based on the electrocardiographic waveform input to the waveform input unit 46. The trigger detection unit 52*b* detects, for example, the position of a peak of an R wave in the electrocardiographic waveform as the trigger point. For example, the trigger detection unit 52*b* measures the peak height of the R wave in the electrocardiographic waveform, and detects the peak position of a next R wave when the potential reaches 80% of the measured peak height. The trigger detection unit 52*b* may generate a filtered waveform obtained by extracting high frequency components of the electrocardiographic waveform by using a band-pass filter, and may detect the trigger point based on a peak position of the filtered waveform. The trigger detection unit 52*b* may exclude a peak position considered to be caused by an arrhythmia from the trigger point, based on an interval between the peak positions of the R wave.

Figure 6:
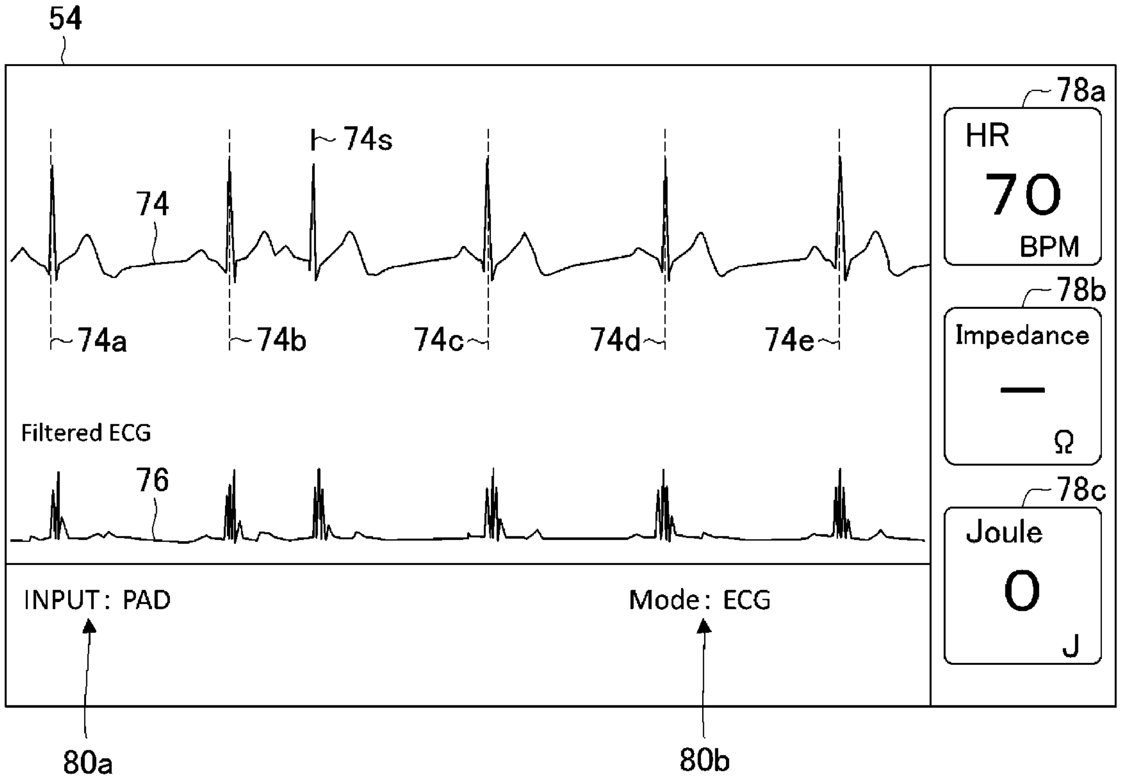
FIG. 6 is a diagram illustrating an example of a display screen of the defibrillation control device.

FIG. 6 is a diagram illustrating an example of a display screen of the defibrillation control device 14, and is a screen example displayed on the display unit 54. In the example illustrated in FIG. 6, the display unit 54 displays an input electrocardiographic waveform 74, a filtered waveform 76, a heartbeat 78*a*, an impedance 78*b*, a joule 78*c*, an input type 80*a*, and a mode 80*b*. The display unit 54 is configured by a liquid crystal display, an organic display, or the like.

The input electrocardiographic waveform 74 is an electrocardiographic waveform input to the waveform input unit 46. The filtered waveform (Filtered ECG) 76 is a waveform of a high frequency component of the input electrocardiographic waveform 74, and is displayed below the input electrocardiographic waveform 74. On the input electrocardiographic waveform 74, trigger markers 74*a*, 74*b*, 74*c*, 74*d*, and 74*e* indicating the positions of trigger points detected by the trigger detection unit 52*b* are displayed in a superimposed manner. The positions of the trigger markers 74*a* to 74*e* correspond to the peak positions of an R wave of the input electrocardiographic waveform 74. In the example of FIG. 6, a skip marker 74*s* indicating a peak position of an R wave not detected as a trigger point is displayed. In the example of FIG. 6, since a time interval from the position of the immediately preceding trigger marker 74*b* to the skip marker 74*s* is shorter than the heartbeat, a peak waveform corresponding to the skip marker 74*s* is excluded from the trigger points.

The heartbeat 78*a* indicates a heart rate calculated from the input electrocardiographic waveform 74. The impedance 78*b* indicates an impedance value measured by the measurement circuit 48*a*. The joule 78*c* indicates the value of electrical energy charged in the capacitor 48*d*.

The input type 80*a* indicates the type of the input electrocardiographic waveform 74. In the example illustrated in FIG. 6, "PAD" indicating an electrocardiographic waveform from the electrode pad 18 is displayed. The mode 80*b* indicates a current operation mode of the defibrillation control device 14. In the example illustrated in FIG. 6, "ECG" indicating that the current operation mode is the cardiac potential measurement mode is displayed. When the current operation mode is the defibrillation mode, "DC" is displayed.

The abnormality detection unit 52*c* detects an earliest abnormal waveform in the abnormality detection mode 70*b*. The abnormality detection unit 52*c* detects an earliest waveform by using a plurality of electrocardiographic waveforms measured by the plurality of electrodes of the electrode catheter 12. More specifically, the abnormality detection unit 52*c* detects an earliest waveform having the earliest timing at which a significant waveform is generated among the first electrocardiographic waveform, the second electrocardiographic waveform, and the third electrocardiographic waveform measured by the first electrode group 31G, the second electrode group 32G, and the third electrode group 33G. Based on the detected earliest waveform, the abnormality detection unit 52*c* detects an earliest abnormal waveform.

Figure 7:
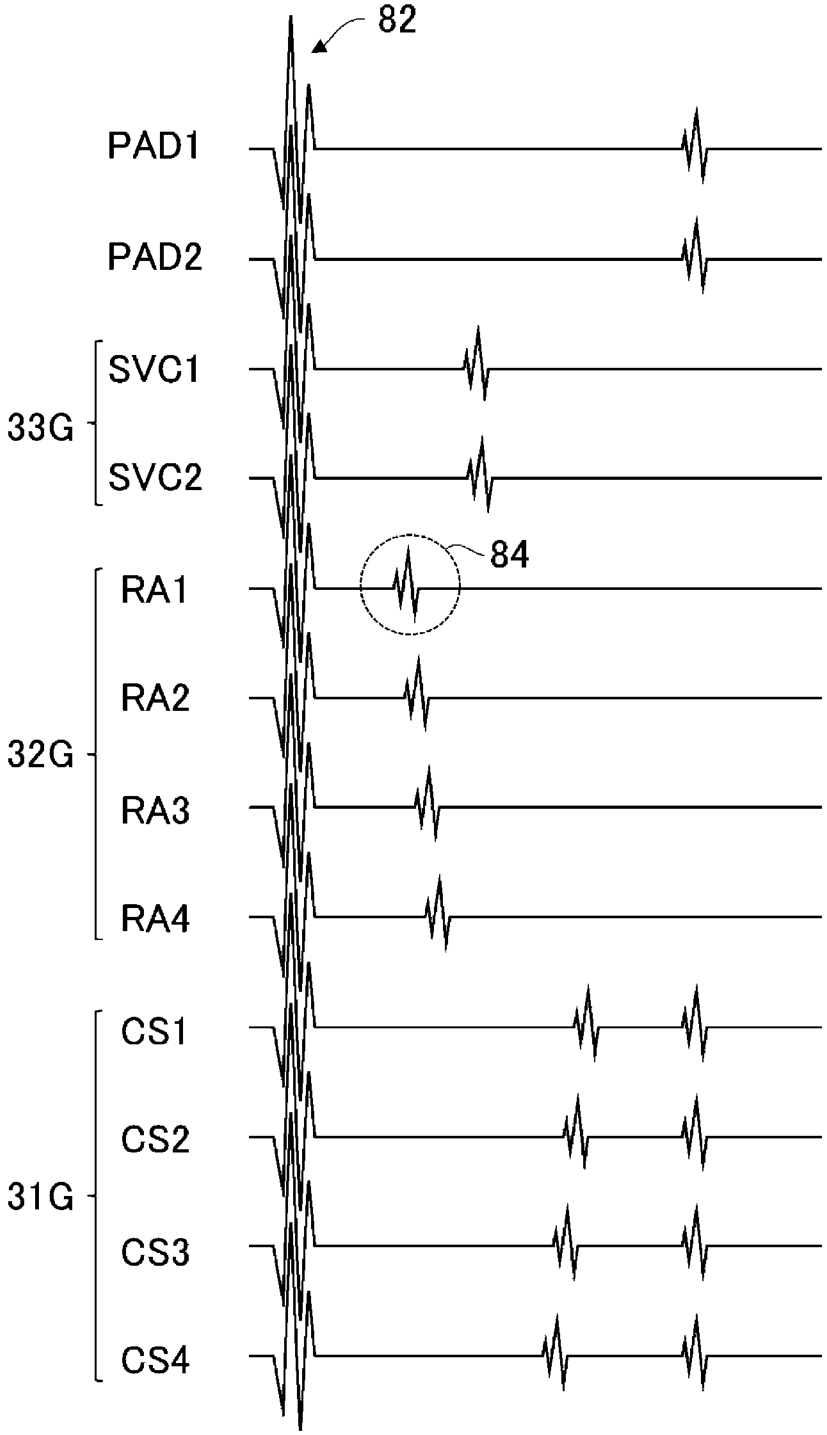
FIG. 7 is a diagram schematically illustrating an example of a plurality of electrocardiographic waveforms during normal operation.

FIG. 7 is a diagram schematically illustrating an example of a plurality of electrocardiographic waveforms during normal operation. The example of FIG. 7 illustrates electrocardiographic waveforms PAD1 and PAD2 measured by the electrode pad 18, two third electrocardiographic waveforms SVC1 and SVC2 measured by the third electrode group 33G, four second electrocardiographic waveforms RA1 to RA4 measured by the second electrode group 32G, and four first electrocardiographic waveforms CS1 to CS4 measured by the first electrode group 31G. At the left end of FIG. 7, a defibrillation waveform 82 with a large amplitude corresponding to an applied voltage for defibrillation is displayed. After the defibrillation waveform 82, an earliest waveform 84 is generated in the RA1, followed by the waveforms in the order of RA2, RA3, RA4, SVC1, SVC2, CS4, CS3, CS2, and CS1. This corresponds to the order of normal electrical signal transmission paths in the cardiac cavity.

Figure 8:
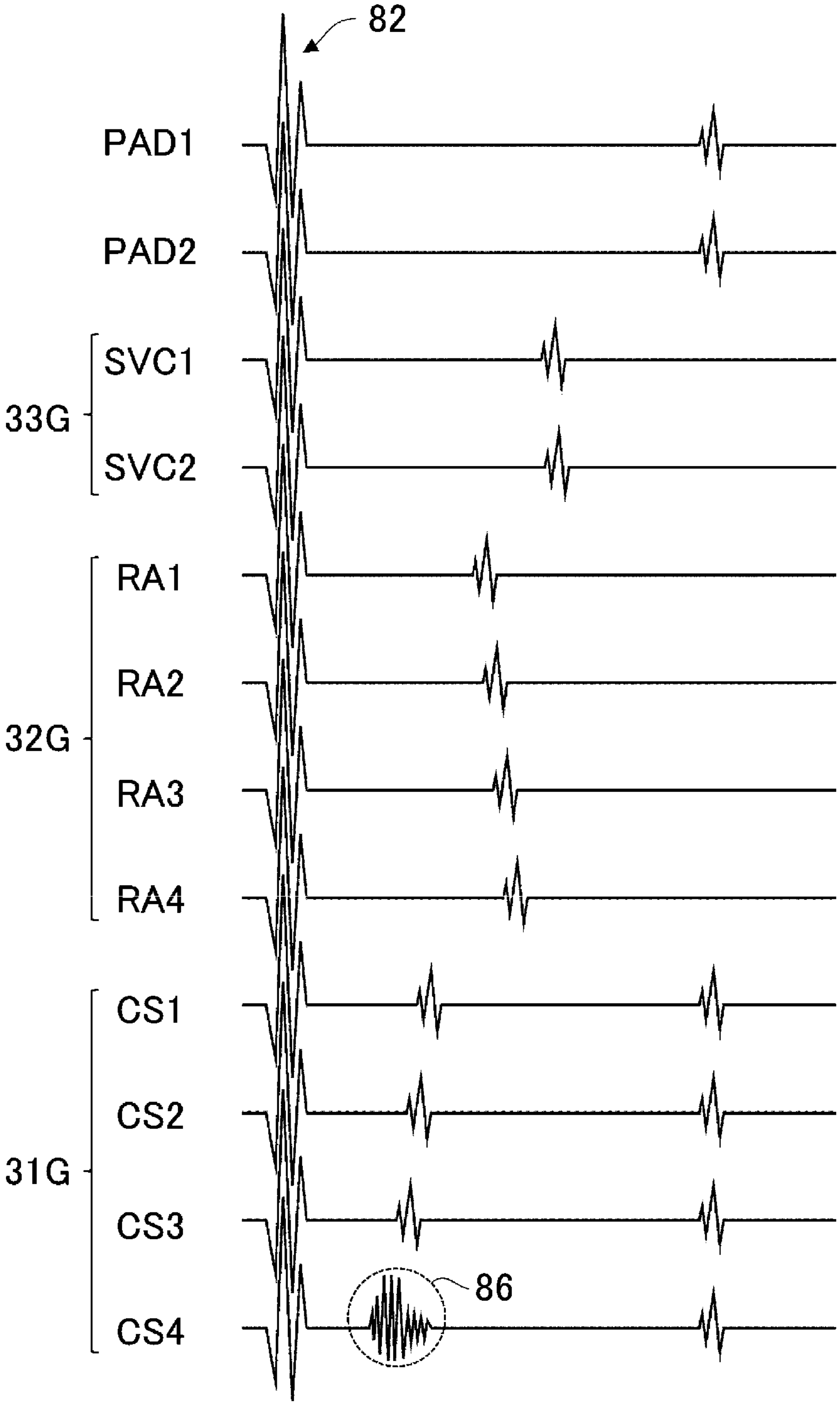
FIG. 8 is a diagram schematically illustrating an example of a plurality of electrocardiographic waveforms during an earliest abnormal time.

FIG. 8 is a diagram schematically illustrating an example of a plurality of electrocardiographic waveforms during the earliest abnormal time. In the example of FIG. 8, after the defibrillation waveform 82, an earliest waveform 86 is generated in the CS4, followed by the waveforms in the order of CS3, CS2, CS1, RA1, RA2, RA3, RA4, SVC1, and SVC2. Consequently, in the example of FIG. 8, the waveforms are generated in an order different from the order during the normal operation illustrated in FIG. 7. This is considered to be because abnormal excitation occurs in the vicinity of the first electrode 31 corresponding to the CS4 and an electrical signal generated at an abnormal excitation site is transmitted to the surroundings. The earliest waveform 86 illustrated in FIG. 8 is different in shape from the earliest waveform 84 illustrated in FIG. 7 due to the abnormal excitation. The earliest waveform 84 of FIG. 7 can be referred to as an earliest normal waveform, and the earliest waveform 86 of FIG. 8 can be referred to as an earliest abnormal waveform.

The abnormality detection unit 52*c* detects the earliest waveform 84 or 86 generated after the defibrillation waveform 82. The abnormality detection unit 52*c* detects, as an earliest waveform among the plurality of electrocardiographic waveforms, a waveform having the earliest start timing at which an amplitude is equal to or greater than a first threshold value (for example, 0.5 mV) after the supplying of the electrical energy. The abnormality detection unit 52*c* detects an earliest abnormal waveform when the detected earliest waveform is not measured by a predetermined electrode (for example, the second electrode 32 corresponding to the RA1) or a predetermined electrode group (for example, the second electrode group 32G).

The abnormality detection unit 52*c* may also detect start timings at which the amplitudes of two or more of the plurality of electrocardiographic waveforms are equal to or greater than the first threshold value (for example, 0.5 mV) after the supplying of the electrical energy, and detect an earliest abnormality by using the detection order of the start timings. The abnormality detection unit 52*c* may also detect the earliest abnormal waveform when the detection order of the start timings of two or more of the plurality of electrocardiographic waveforms does not match a predetermined order of the electrodes (for example, RA1, RA2, RA3, RA4, SVC1, SVC2, CS4, CS3, CS2, and CS1). The abnormality detection unit 52*c* may also detect the earliest abnormal waveform when the detection order of the start timings of two or more of the plurality of electrocardiographic waveforms does not match a predetermined order of the electrode groups (for example, the second electrode group 32G, the third electrode group 33G, and the first electrode group 31G).

Figure 9:
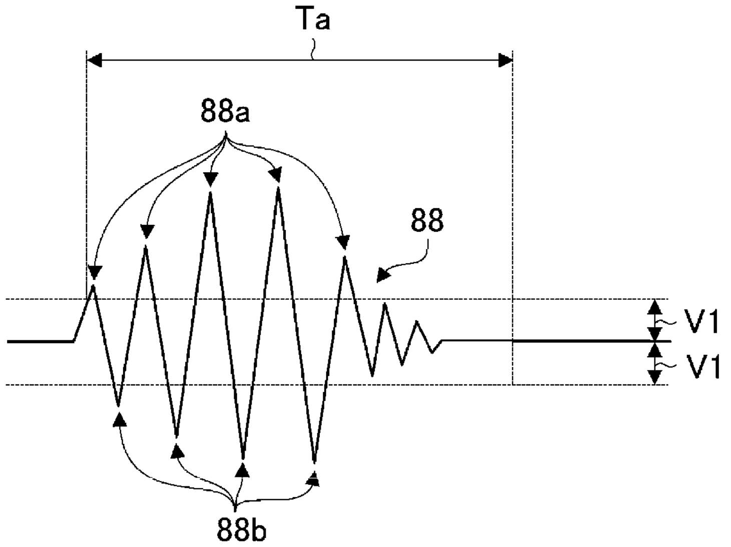
FIG. 9 is a diagram schematically illustrating an example of an earliest abnormal waveform.
Figure 10:
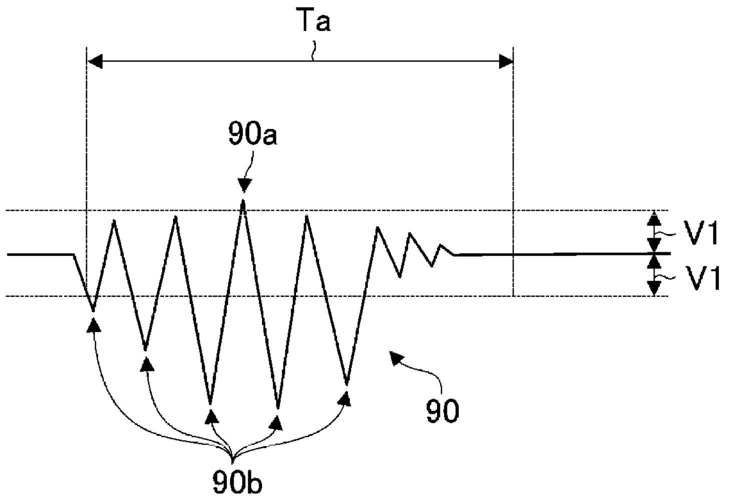
FIG. 10 is a diagram schematically illustrating an example of an earliest abnormal waveform.
Figure 11:
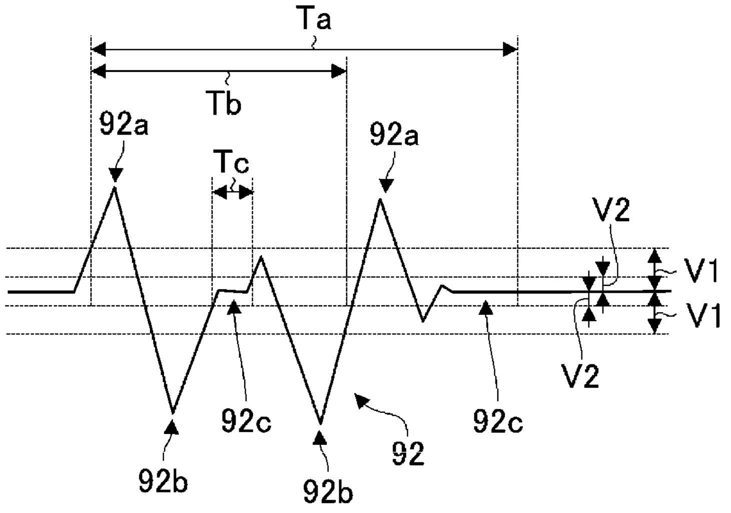
FIG. 11 is a diagram schematically illustrating an example of an earliest abnormal waveform.

When the shape of the detected earliest waveform matches a predetermined abnormal shape, the abnormality detection unit 52*c* detects the earliest abnormal waveform. FIGS. 9 to 11 are diagrams schematically illustrating an example of earliest abnormal waveforms 88, 90, and 92. FIG. 9 illustrates the earliest abnormal waveform 88 corresponding to a first abnormal shape. The condition of the first abnormal shape is that during a period from the start timing of an earliest waveform until a first reference time Ta elapses (for example, 150 ms), the number of detected waveform portions 88*a* and 88*b*, in which an amplitude of the waveform is equal to or greater than the first threshold value V1 (for example, 0.5 mV), is equal to or greater than a predetermined first number (for example, eight). The starting point of the first reference time Ta is a timing at which the amplitude of the earliest waveform first reaches the first threshold value V1. The starting point of the first reference time Ta may be a timing at which the amplitude of the waveform is upward and reaches the first threshold value V1, or may be a timing at which the amplitude of the waveform is downward and reaches the first threshold value V1. The number of detected waveform portions equal to or greater than the first threshold value V1 is the sum of the number of upward waveform portions 88*a* equal to or greater than the first threshold value V1 and the number of downward waveform portions 88*b* equal to or greater than the first threshold value V1. In the example illustrated in FIG. 9, since the number of upward waveform portions 88*a* is five, the number of downward waveform portions 88*b* is four, and the total number of detected waveform portions is nine and is equal to or greater than the predetermined number (for example, eight), the upward waveform portions 88*a* and the downward waveform portions 88*b* match the first abnormal shape.

FIG. 10 illustrates the earliest abnormal waveform 90 corresponding to a second abnormal shape. The condition of the second abnormal shape is that during a period from the start timing of an earliest waveform until the first reference time Ta elapses (for example, 150 ms), the number of detected downward waveform portions 90*b*, in which an amplitude of the waveform is equal to or greater than the first threshold value V1 (for example, 0.5 mV), is equal to or greater than a predetermined second number (for example, five). The second number (for example, five) related to the second abnormal shape is smaller than the first number (for example, eight) related to the first abnormal shape. The starting point of the first reference time Ta is the same as the starting point of the first abnormal shape in FIG. 9, and may be a timing at which the amplitude of the waveform is upward and reaches the first threshold value V1, or may be a timing at which the amplitude of the waveform is downward and reaches the first threshold value V1. In the example illustrated in FIG. 10, since the number of upward waveform portions 90*a* is one, the number of downward waveform portions 90*b* is five, and the total number of detected waveform portions is six and is smaller than the first number (for example, eight), the downward waveform portion 90*b* does not match the first abnormal shape. However, since the number of downward waveform portions 90*b* is equal to or greater than the predetermined number (for example, five), the downward waveform portion 90*b* matches the second abnormal shape.

FIG. 11 illustrates the earliest abnormal waveform 92 corresponding to a third abnormal shape. The condition of the third abnormal shape is that during a period from the start timing of an earliest waveform until a second reference time Tb (for example, 90 ms) elapses, a continuous time Tc of a flat portion 92*c* in which an amplitude of the waveform is equal to or less than a second threshold time V2 (for example, 0.2 mV) smaller than the first threshold time V1 does not exceed a predetermined value (for example, 20 ms). It can also be said that the condition of the third abnormal waveform is that the time length of one waveform range constituting the earliest waveform is equal to or longer than the second reference time Tb (for example, 90 ms). The one waveform range ends when the continuous time Tc of the flat portion 92*c* exceeds the predetermined value (for example, 20 ms). In other words, when the continuous time Tc of the flat portion 92*c* is equal to or less than the predetermined value (for example, 20 ms), waveforms before and after the flat portion 92*c* are regarded as one waveform range. In the example illustrated in FIG. 11, since the continuous time Tc of the flat portion 92*c* is not equal to or greater than the predetermined value (for example, 20 ms) during the period from the start timing of the earliest waveform until the second reference time Tb elapses (for example, 90 ms), the flat portion 92*c* matches the third abnormal shape. In the example illustrated in FIG. 11, since the number of upward waveform portions 92*a* is two and the number of downward waveform portions 92*b* is two, the upward waveform portions 92*a* and the downward waveform portions 92*b* match neither the first abnormal shape nor the second abnormal shape.

The abnormality detection unit 52*c* may further detect cardiac arrest in the abnormality detection mode 70*b*. The abnormality detection unit 52*c* detects cardiac arrest when the number of heartbeats for which the amplitude of the waveform is equal to or greater than a third threshold value V3 (for example, 2.8 mV) is less than five during a period from the elapse of a first time (for example, 5 seconds) after the completion of discharge for defibrillation until a second time elapses (for example, 10 seconds). The abnormality detection unit 52*c* ends the cardiac arrest detection process when the number of heartbeats for which the amplitude of the waveform is equal to or greater than the third threshold value V3 (for example, 2.8 mV) is less than five before the elapse of the second time (for example, 10 seconds) after the elapse of the first time (for example, 5 seconds) since the completion of the discharge for defibrillation.

When an abnormality is detected by the abnormality detection unit 52*d*, the warning unit 52*c* issues an alert. When the earliest abnormal waveform or cardiac arrest is detected by the abnormality detection unit 52*c*, the warning unit 52*d* causes the display unit 54 to display an alert and causes the speaker 56 to output a warning sound. The warning unit 52*d* may cause the display unit 54 to display information indicating an electrocardiographic waveform, an electrode group, or an electrode from which the earliest abnormal waveform has been detected. For example, in the example of FIG. 8, "CS4" indicating an electrocardiographic waveform from which the earliest abnormal waveform 86 is detected may be displayed, "CS" indicating an electrode group may be displayed, or "7" and "8" indicating electrode numbers may be displayed. When a predetermined button of the operation button 50 for stopping the alert is operated, the warning unit 52*d* stops the warning display and the warning sound.

Referring back to FIG. 1, the monitoring device 16 is described. The monitoring device 16 includes a waveform acquisition unit 60, a waveform providing unit 62, and a waveform selection unit 64.

The waveform acquisition unit 60 acquires the electrocardiographic waveform of the patient 20. The waveform acquisition unit 60 acquires the first electrocardiographic waveform, the second electrocardiographic waveform, and the third electrocardiographic waveform output from the waveform output unit 44 of the defibrillation control device 14. The waveform acquisition unit 60 acquires the body surface electrocardiographic waveform of the patient 20 measured using the electrode pad 18. When another electrode catheter different from the electrode catheter 12 is used for the patient 20, the waveform acquisition unit 60 acquires an electrocardiographic waveform (also referred to as a fourth electrocardiographic waveform) measured using the other electrode catheter.

The waveform providing unit 62 provides the waveform input unit 46 of the defibrillation control device 14 with at least one of the electrocardiographic waveforms acquired by the waveform acquisition unit 60. The waveform selection unit 64 selects an electrocardiographic waveform provided by the waveform providing unit 62 in response to a user operation. For example, when the waveform selection unit 64 selects the body surface electrocardiographic waveform from the electrode pad 18, the waveform providing unit 62 provides the selected body surface electrocardiographic waveform to the defibrillation control device 14.

Figure 12:
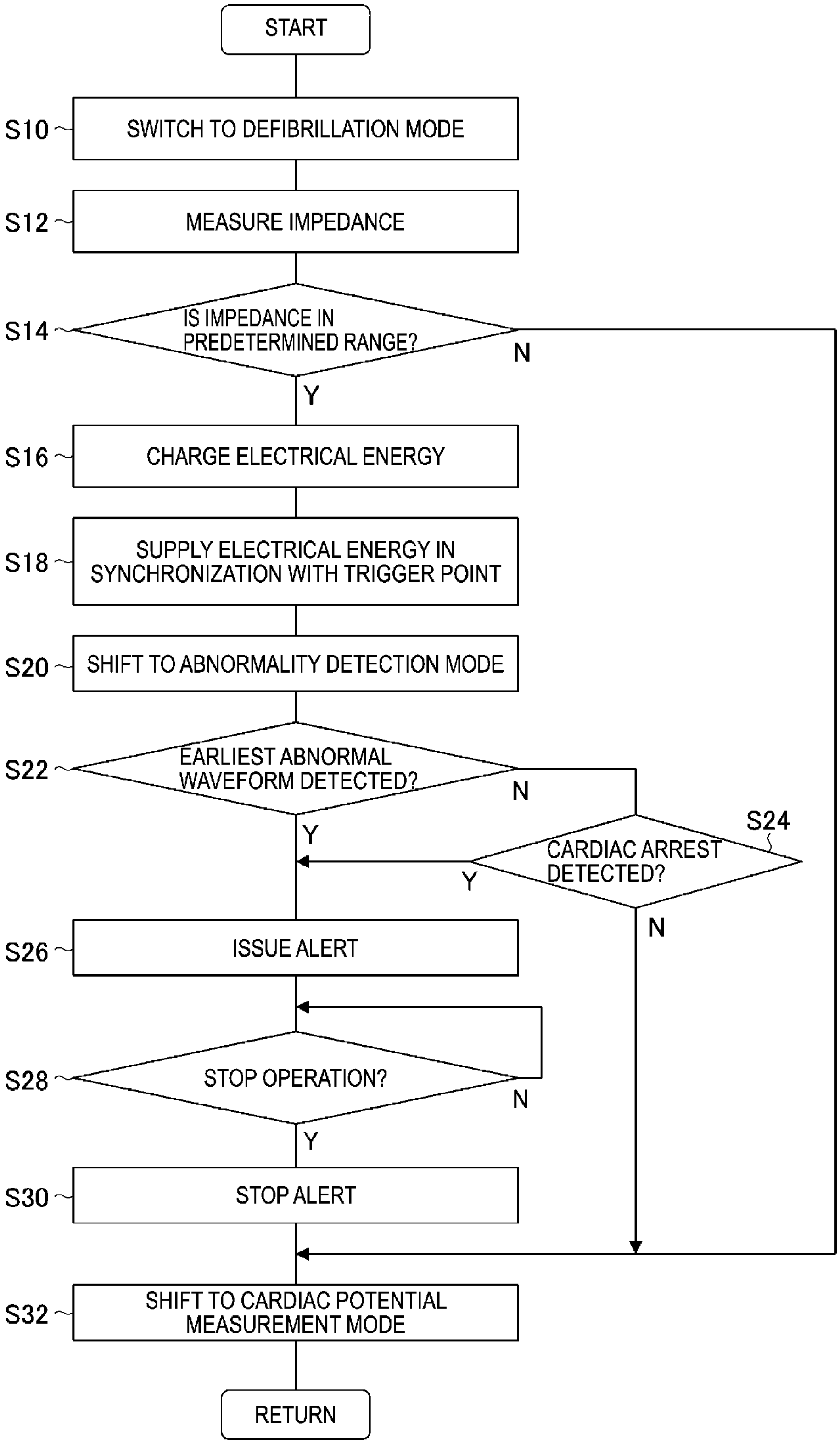
FIG. 12 is a flowchart schematically showing a defibrillation method according to the first embodiment.

FIG. 12 is a flowchart schematically showing a defibrillation method according to the first embodiment. First, the mode switching button 50*a* is pressed in the cardiac potential measurement mode so that the operation mode is switched to the defibrillation mode (step S10). Subsequently, an impedance between the electrodes of the electrode catheter 12 is measured (step S12), and when the impedance is within a predetermined range (Y in step S14), electrical energy is charged upon pressing the charging button 50*b* (step S16). After completion of charging with the electrical energy, the electrical energy is supplied to the electrode catheter 12 in synchronization with a trigger point upon pressing the discharge button 50*c* (step S18). After the supplying of the electrical energy is completed, the operation mode is shifted to the abnormality detection mode (step S20).

In the abnormality detection mode, when an earliest abnormal waveform is detected (Y in step S22), an alert is issued (step S26). When no earliest abnormal waveform is detected (N in step S22) and cardiac arrest is detected (Y in step S24), an alert is issued (step S26). The alert is continued until a predetermined stop operation is performed by a user (N in step S28). When the predetermined stop operation is performed by the user (Y in step S28), the alert is stopped (step S30) and the operation mode is shifted to the cardiac potential measurement mode (step S32). In step S14, when the impedance is out of the predetermined range (N in step S14), the operation mode is shifted to the cardiac potential measurement mode (step S32). In step S24, when no cardiac arrest is detected (N in step S24), steps S26, S28, and S30 are skipped, and the operation mode is shifted to the cardiac potential measurement mode (step S32).

According to the present embodiment, by shifting to the abnormality detection mode after completion of defibrillation, an earliest abnormal waveform can be detected using a plurality of electrocardiographic waveforms measured by the electrode catheter. By issuing an alert upon detecting the earliest abnormal waveform, useful information can be quickly notified to a user such as a doctor.

According to the present embodiment, various types of earliest abnormal waveforms can be detected by analyzing the shape and electrode position of the detected earliest waveform. For example, by determining whether the shape of a detected earliest waveform matches any one of the first abnormal shape, the second abnormal shape, and the third abnormal shape, earliest abnormal waveforms with various shapes can be detected.

According to the present embodiment, by notifying information on the electrode position of the detected earliest abnormal waveform, information on an abnormal excitation site considered to be a cause of the earliest abnormal waveform can be notified. In the ablation treatment, since an abnormal excitation site is required to be appropriately specified, useful information can be provided to a user such as a doctor.

Second Embodiment

Figure 13:
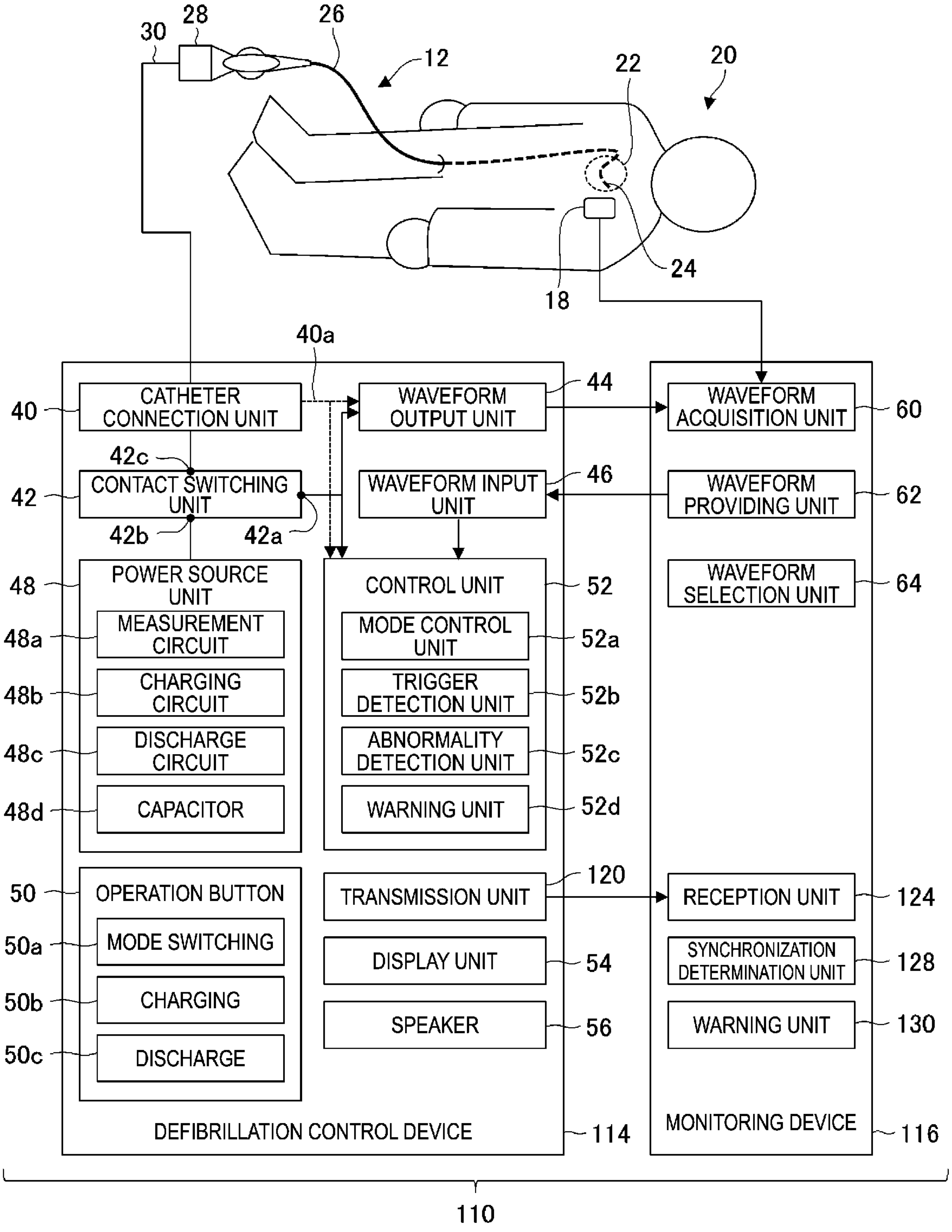
FIG. 13 is a diagram schematically illustrating a configuration of a defibrillation system according to a second embodiment.

FIG. 13 is a diagram schematically illustrating a configuration of a defibrillation system 110 according to a second embodiment. In the second embodiment, a defibrillation control device 114 further includes a transmission unit 120, and a monitoring device 116 further includes a reception unit 124, a synchronization determination unit 128, and a warning unit 130. The second embodiment is described below with a focus on differences from the first embodiment, and description of common points is appropriately omitted.

The defibrillation system 110 includes an electrode catheter 12, the defibrillation control device 114, and the monitoring device 116. The electrode catheter 12 is configured similarly to the first embodiment.

The defibrillation control device 114 includes a catheter connection unit 40, a contact switching unit 42, a waveform output unit 44, a waveform input unit 46, a power source unit 48, an operation button 50, a control unit 52, a display unit 54, a speaker 56, and a transmission unit 120.

The transmission unit 120 transmits a trigger signal indicating a trigger point detected by a trigger detection unit 52*b* to the monitoring device 116. When the trigger point is not detectable by the trigger detection unit 52*b*, the transmission unit 120 transmits a trigger abnormal signal to the monitoring device 116. The reason why the trigger point is not detectable may be that no electrocardiographic waveform is input to the waveform input unit 46, or an electrocardiographic waveform input to the waveform input unit 46 is abnormal and the peak of an R wave is not detectable.

The monitoring device 116 includes a waveform acquisition unit 60, a waveform providing unit 62, a waveform selection unit 64, a reception unit 124, a synchronization determination unit 128, and a warning unit 130.

The reception unit 124 receives a signal transmitted from the transmission unit 120 of the defibrillation control device 114. The reception unit 124 receives the trigger signal. The reception unit 124 receives the trigger abnormal signal.

The synchronization determination unit 128 determines whether the trigger signal received by the reception unit 124 and an electrocardiographic waveform provided by the waveform providing unit 62 are synchronized with each other. The trigger detection unit 52*b* of the defibrillation control device 114 detects a trigger point by using the electrocardiographic waveform provided from the waveform providing unit 62. Therefore, by determining the synchronization between the trigger signal and the electrocardiographic waveform, whether the trigger detection unit 52*b* appropriately detects the trigger point can be confirmed.

For example, the synchronization determination unit 128 detects the peak position of an R wave of the electrocardiographic waveform by using the same method as the method of the trigger detection unit 52*b*, and determines whether the detection timing and the trigger signal are synchronized with each other. The synchronization determination unit 128 may also determine the synchronization between the electrocardiographic waveform and the trigger signal by using a method different from the method of the trigger detection unit 52*b*.

When the reception unit 124 receives the trigger abnormal signal, the warning unit 130 issues an alert. When the synchronization determination unit 128 determines that the trigger signal is not synchronized, the warning unit 130 issues an alert. The warning unit 130 issues an alert by, for example, a warning display on a display screen of the monitoring device 116 or a warning sound from a speaker of the monitoring device 116. When a predetermined operation for stopping the alert is performed, the warning unit 130 stops the alert by the warning display and the warning sound.

When the alert is issued by the warning unit 130, a user can perform an operation of switching the electrocardiographic waveform selected by the waveform selection unit 64 to another electrocardiographic waveform after stopping the alert. The user can select any one of a plurality of electrocardiographic waveforms acquired by the waveform acquisition unit 60. For example, an operation of switching the electrocardiographic waveform selected by the waveform selection unit 64 from PAD1 to PAD2 can be performed.

Figure 14:
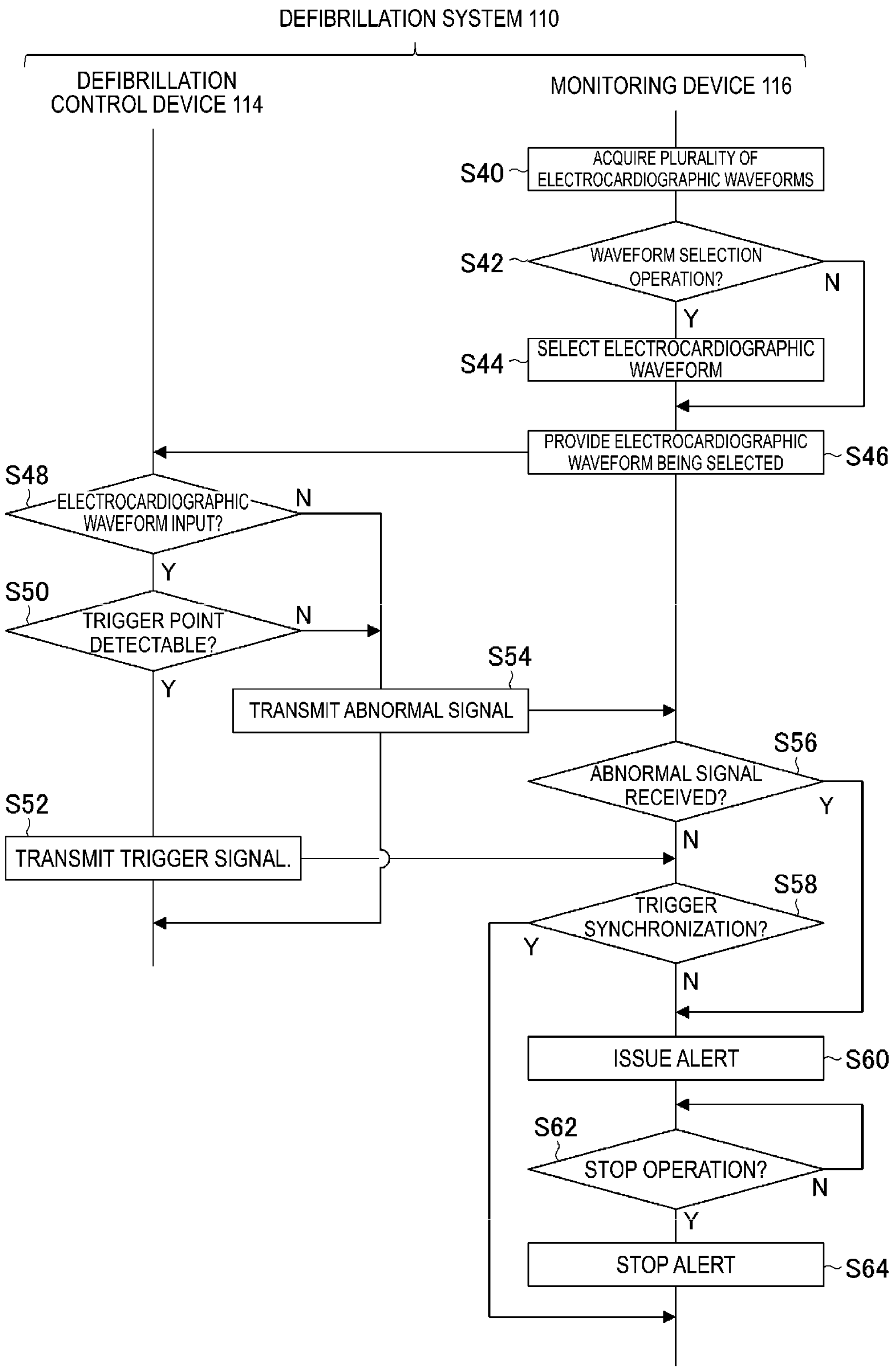
FIG. 14 is a flowchart schematically showing a trigger detection method according to the second embodiment.

FIG. 14 is a flowchart schematically illustrating a trigger detection method according to the second embodiment. The monitoring device 116 acquires a plurality of electrocardiographic waveforms by the waveform acquisition unit 60 (step S40). When a waveform selection operation is performed by the user (Y in step S42), one of the plurality of electrocardiographic waveforms is selected by the waveform selection unit 64 in accordance with the selection operation (step S44). When no waveform selection operation is performed (N in step S42), the process of step S44 is skipped. The monitoring device 116 provides an electrocardiographic waveform being selected from the waveform providing unit 62 to the defibrillation control device 114 (step S46).

When the electrocardiographic waveform is input (Y in step S48) and a trigger point is detectable by the trigger detection unit 52*b* (Y in step S50), the defibrillation control device 114 transmits a trigger signal from the transmission unit 120 to the monitoring device 116 (step S52).

When no electrocardiographic waveform is input (N in step S48) or when no trigger point is not detectable by the trigger detection unit 52*b* (N in step S50), the defibrillation control device 114 transmits a trigger abnormal signal from the transmission unit 120 to the monitoring device 116 (step S54).

When the reception unit 124 receives the trigger abnormal signal (Y in step S56), the monitoring device 116 causes the warning unit 130 to issue an alert (step S60). When no trigger abnormal signal is received (N in step S56) and the synchronization determination unit 128 determines that the trigger signal is not synchronized (N in step S58), the monitoring device 116 causes the warning unit 130 to issue an alert (step S60). The monitoring device 116 continues the alert by the warning unit 130 until a predetermined stop operation is performed by the user (N in step S62), and stops the alert by the warning unit 130 (step S64) when the predetermined stop operation is performed by the user (Y in step S62). In step S58, when the synchronization determination unit 128 determines that the trigger signal is synchronized (Y in step S58), the processes of steps S60, S62, and S64 are skipped.

The flow of FIG. 14 is repeatedly performed. After the alert is stopped in step S64, the user performs a waveform selection operation for selecting an electrocardiographic waveform different from the electrocardiographic waveform being selected. In this case, the process of step S42 is Y, the electrocardiographic waveform being selected is switched to another electrocardiographic waveform (step S44), and the switched electrocardiographic waveform is provided to the defibrillation control device 114 (step S46).

According to the present embodiment, when no trigger point is detectable by the defibrillation control device 114, an alert can be issued by the monitoring device 116 instead of the defibrillation control device 114. When an alert is issued by the defibrillation control device 114, the user needs to perform an electrocardiographic waveform switching operation by the monitoring device 116 after performing an alert stop operation by the defibrillation control device 114, causing time and effort to operate each of the two devices. On the other hand, when the alert is issued by the monitoring device 116, the user can perform the electrocardiographic waveform switching operation by the monitoring device 116 after the alert stop operation of the monitoring device 116 so that only one device needs to operate. According to the present embodiment, convenience for the user who uses the defibrillation system 110 can be improved. In particular, in urgent situations requiring defibrillation treatment, reducing a burden on the user even a little is very beneficial.

As a modified example of the second embodiment, instead of causing the monitoring device 116 to issue an alert, the waveform selection unit 64 may automatically switch an electrocardiographic waveform being selected to another electrocardiographic waveform. The waveform selection unit 64 may record the status of "unselected" or "selected" for each of the plurality of electrocardiographic waveforms acquired by the waveform acquisition unit 60. When an electrocardiographic waveform is selected, the waveform selection unit 64 updates the status of the selected electrocardiographic waveform from "unselected" to "selected". When an electrocardiographic waveform is automatically selected, the waveform selection unit 64 selects any one of unselected electrocardiographic waveforms. When no unselected electrocardiographic waveform is present and the waveform selection unit 64 is not able to automatically select an unselected electrocardiographic waveform, the warning unit 130 issues an alert.

Figure 15:
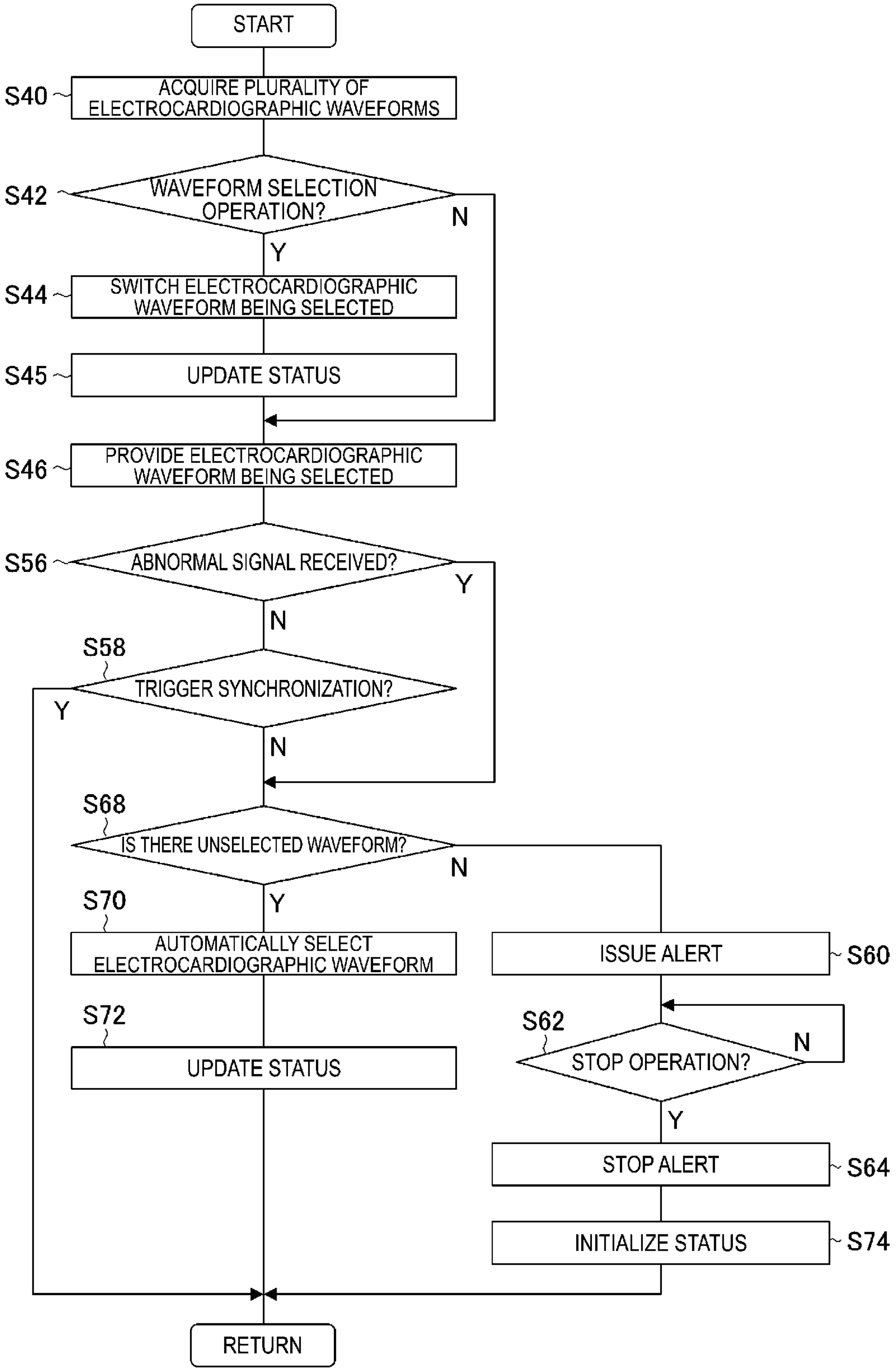
FIG. 15 is a flowchart schematically showing a waveform selection method according to the second embodiment.

FIG. 15 is a flowchart schematically illustrating a waveform selection method according to the second embodiment. The flow of FIG. 15 shows only the operation of the monitoring device 116. In the flow of FIG. 15, the operation of the defibrillation control device 114 is the same as the operation of the flow of FIG. 14. In the flow of FIG. 15, the same processes as the processes in the flow of FIG. 14 are denoted by the same reference numerals.

The monitoring device 116 performs the same processes as steps S40, S42, S44, and S46 in FIG. 14, but updates the status of a selected electrocardiographic waveform to "selected" after the execution of step S44 (step S45). When the reception unit 124 receives a trigger abnormal signal (Y in step S56) and electrocardiographic waveforms with the status of "unselected" are present (Y in step S68), the monitoring device 116 causes the waveform selection unit 64 to automatically select one of the "unselected" electrocardiographic waveforms (step S70). When no trigger abnormal signal is received (N in step S56) and the synchronization determination unit 128 determines that the trigger signal is not synchronized (N in step S58), the monitoring device 116 performs the process of step S70 when the electrocardiographic waveforms with the status of "unselected" are present (Y in step S68). The status of the electrocardiographic waveform automatically selected by the waveform selection unit 64 is updated to "selected" by the waveform selection unit 64 (step S72). When no electrocardiographic waveforms with the status of "unselected" are present in step S68 (N in step S68), the monitoring device 116 performs the processes of steps S60, S62, and S64 in FIG. 14, and then performs initialization for setting all the statuses of the plurality of electrocardiographic waveforms to "unselected" (step S74).

According to the processing flow of FIG. 15, when the defibrillation control device 114 is not able to detect a trigger point, the electrocardiographic waveform being selected by the monitoring device 116 is automatically switched so that the time and effort of a selection operation for switching an electrocardiographic waveform can be saved. Thus, convenience for a user who uses the defibrillation system 110 can be improved.

Third Embodiment

Figure 16:
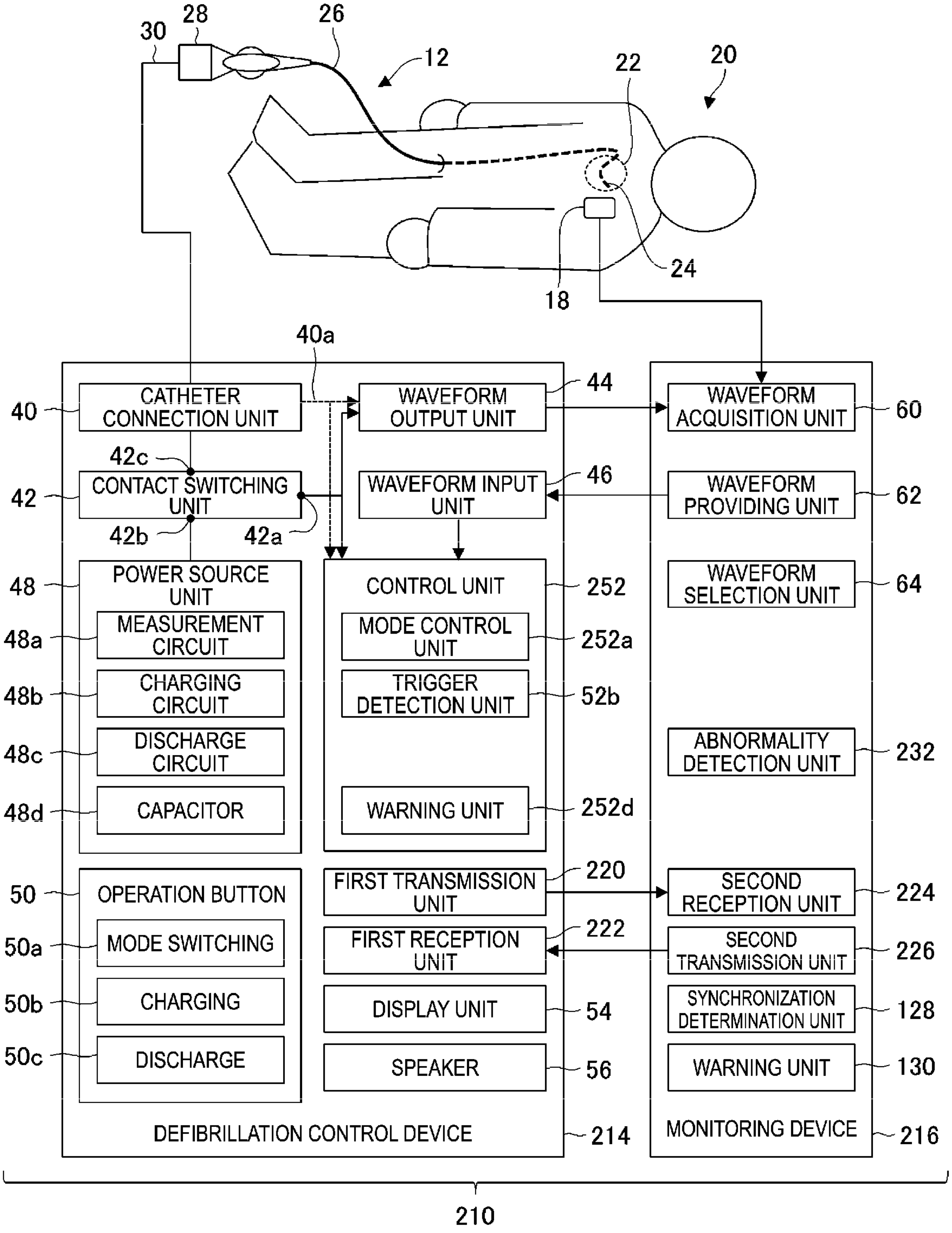
FIG. 16 is a diagram schematically illustrating a configuration of a defibrillation system according to a third embodiment.

FIG. 16 is a diagram schematically illustrating a configuration of a defibrillation system 210 according to a third embodiment. In the third embodiment, a monitoring device 216 is provided with an abnormality detection unit 232 that detects an earliest abnormal waveform or cardiac arrest. The third embodiment is described below with a focus on differences from the embodiments described above, and description of common points is appropriately omitted.

The defibrillation system 210 includes an electrode catheter 12, a defibrillation control device 214, and a monitoring device 216. The electrode catheter 12 is configured similarly to the first embodiment.

The defibrillation control device 214 includes a catheter connection unit 40, a contact switching unit 42, a waveform output unit 44, a waveform input unit 46, a power source unit 48, an operation button 50, a control unit 252, a display unit 54, a speaker 56, a first transmission unit 220, and a first reception unit 222.

The control unit 252 includes a mode control unit 252*a*, a trigger detection unit 52*b*, and a warning unit 252*d*. The control unit 252 is different from the first embodiment in that the abnormality detection unit 52*c* is not provided.

The mode control unit 252*a* is different from the first embodiment in that the abnormality detection mode 70*b* of FIG. 5 is not provided. When the supplying of electrical energy is completed in the discharge mode 72*c*, the mode control unit 252*a* shifts to the normal mode 70*a*.

When the first reception unit 222 receives an abnormal signal from the monitoring device 216, the warning unit 252*d* issues an alert. When a predetermined button operation for stopping the alert is performed, the warning unit 252*d* stops a warning display and a warning sound.

When the supplying of the electrical energy is completed in the discharge mode 72*c*, the first transmission unit 220 transmits a supply completion signal (or a defibrillation completion signal) to the monitoring device 216. The supply completion signal is transmitted, for example, when the supplying of the electrical energy is completed in the discharge mode 72*c* and the recording of the voltage waveform in the discharge period T illustrated in FIG. 4 is completed.

Similarly to the transmission unit 120 according to the second embodiment, the first transmission unit 220 transmits a trigger signal indicating a trigger point detected by the trigger detection unit 52*b* to the monitoring device 216. Similarly to the transmission unit 120 according to the second embodiment, the first transmission unit 220 transmits a trigger abnormal signal to the monitoring device 216 when no trigger point is detectable by the trigger detection unit 52*b*. The first reception unit 222 receives the abnormal signal from the monitoring device 216. When the first reception unit 222 receives the abnormal signal, an alert is issued by the warning unit 252*d*.

The monitoring device 216 includes a waveform acquisition unit 60, a waveform providing unit 62, a waveform selection unit 64, a second reception unit 224, a second transmission unit 226, an abnormality detection unit 232, a synchronization determination unit 128, and a warning unit 130.

The second reception unit 224 receives the supply completion signal transmitted from the defibrillation control device 214. The second reception unit 224 receives the trigger signal and the trigger abnormal signal transmitted from the defibrillation control device 214. When an earliest abnormal waveform or cardiac arrest is detected by the abnormality detection unit 232, the second transmission unit 226 transmits an abnormal signal to the defibrillation control device 214.

When the second reception unit 224 receives the supply completion signal, the abnormality detection unit 232 detects the earliest abnormal waveform or cardiac arrest by using a plurality of electrocardiographic waveforms acquired by the waveform acquisition unit 60 after the reception of the supply completion signal. The method of detecting the earliest abnormal waveform or cardiac arrest by the abnormality detection unit 232 is the same as the method of detecting the earliest abnormal waveform or cardiac arrest by the abnormality detection unit 52*c* according to the first embodiment described above. Consequently, the abnormality detection unit 232 detects the earliest abnormal waveform or cardiac arrest by using a plurality of electrocardiographic waveforms (for example, the first electrocardiographic waveform, the second electrocardiographic waveform, and the third electrocardiographic waveform) measured by the plurality of electrodes of the electrode catheter 12.

When the earliest abnormal waveform is detected by the abnormality detection unit 232, the second transmission unit 226 may transmit, to the defibrillation control device 214, information indicating an electrocardiographic waveform, an electrode group, or an electrode from which the earliest abnormal waveform is detected. In this case, the warning unit 252*d* may cause the display unit 54 to display the information indicating the electrocardiographic waveform, the electrode group, or the electrodes from which the earliest abnormal waveform is detected, by using information received by the first reception unit 222.

Figure 17:
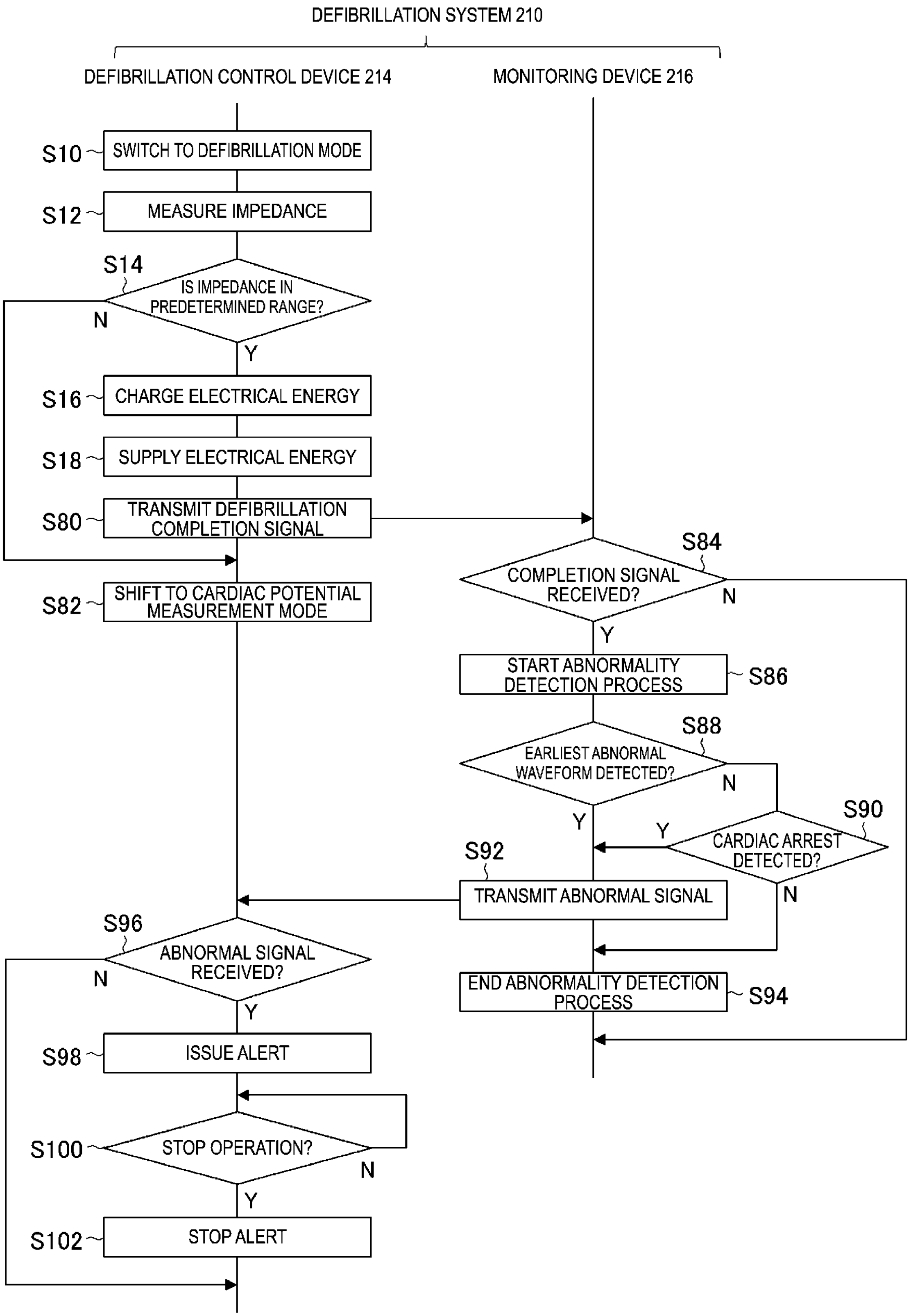
FIG. 17 is a flowchart schematically showing a defibrillation method according to the third embodiment.

FIG. 17 is a flowchart schematically showing a defibrillation method according to the third embodiment. In the flow of FIG. 17, the same processes as the processes in the flow of FIG. 12 are denoted by the same reference numerals.

First, the same processes as the processes of steps S10, S12, S14, S16, and S18 of FIG. 12 are performed. After the supplying of the electrical energy in step S18 is completed, a supply completion signal is transmitted from the first transmission unit 220 to the monitoring device 216 (step S80), and the mode control unit 252*a* shifts the operation mode to the cardiac potential measurement mode (S82). In step S14, when the impedance is out of the predetermined range (N in step S14), the processes of steps S16, S18, and S80 are skipped, and the operation mode is shifted to the cardiac potential measurement mode (step S82).

When the second reception unit 224 receives the supply completion signal (Y in step S84), the monitoring device 216 starts an abnormality detection process by the abnormality detection unit 232 (step S86). When an earliest abnormal waveform is detected by the abnormality detection unit 232 (Y in step S88), the monitoring device 216 transmits an abnormal signal from the second transmission unit 226 to the defibrillation control device 214 (step S92).

When no earliest abnormal waveform is detected by the abnormality detection unit 232 (N in step S88) and cardiac arrest is detected (Y in step S90), the monitoring device 216 transmits an abnormal signal from the second transmission unit 226 to the defibrillation control device 214 (step S92). After the process of step S92, the monitoring device 216 ends the abnormality detection process (step S94). When no cardiac arrest is detected in step S90 (N in step S90), the monitoring device 216 ends the abnormality detection process (step S94). When the supply completion signal is not received in step S84 (N in step S84), the monitoring device 216 skips the processes of steps S86, S88, S90, S92, and S94.

When the first reception unit 222 receives the abnormal signal (Y in step S96), the defibrillation control device 214 issues an alert by the warning unit 252*d* (step S98). The defibrillation control device 214 continues the alert by the warning unit 252*d* until a predetermined stop operation is performed by a user (N in step S100), and stops the alert by the warning unit 252*d* (step S102) when the predetermined stop operation is performed by the user (Y in step S100). When the abnormal signal is not received in step S96 (N in step S96), the processes of steps S98, S100, and S102 are skipped.

According to the present embodiment, even when the defibrillation control device 214 not including the abnormality detection unit 52*c* is used, an abnormality such as an earliest abnormal waveform or cardiac arrest can be detected in the monitoring device 216. According to the present embodiment, when the earliest abnormal waveform or cardiac arrest is detected in the monitoring device 216, an abnormal signal is transmitted from the monitoring device 216 to the defibrillation control device 214 so that the defibrillation control device 214 can issue an alert. When the alert is issued by the defibrillation control device 214, a user can perform an operation for defibrillation again by the defibrillation control device 214 after an alert stop operation of the defibrillation control device 214 so that only one device needs to operate. Consequently, according to the present embodiment, convenience for a user who uses the defibrillation system 210 can be improved. In particular, in urgent situations requiring defibrillation treatment, reducing a burden on the user even a little is very beneficial.

In the third embodiment, the monitoring device 216 need not include the synchronization determination unit 128 and the warning unit 130. In this case, the first transmission unit 220 of the defibrillation control device 214 need not transmit a trigger signal and a trigger point signal to the monitoring device 216.

Fourth Embodiment

Figure 18:
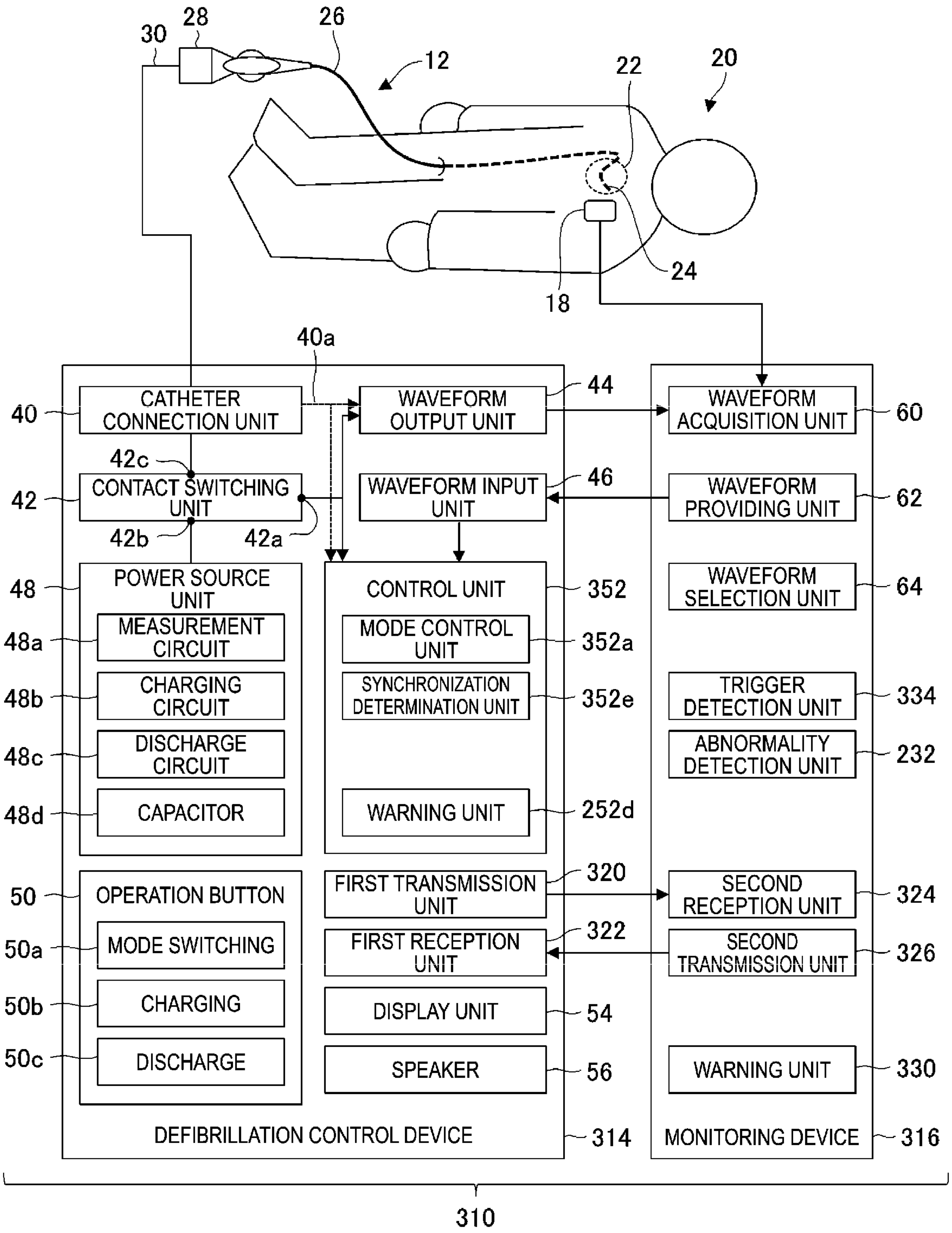
FIG. 18 is a diagram schematically illustrating a configuration of a defibrillation system according to a fourth embodiment.

FIG. 18 is a diagram schematically illustrating a configuration of a defibrillation system 310 according to a fourth embodiment. In the fourth embodiment, a synchronization determination unit 352*e* is provided in a defibrillation control device 314, and a trigger detection unit 334 is provided in a monitoring device 316. The fourth embodiment is described with a focus on differences from the embodiments described above, and description of common points is appropriately omitted.

The defibrillation system 310 includes an electrode catheter 12, the defibrillation control device 314, and the monitoring device 316. The electrode catheter 12 is configured similarly to the first embodiment.

The defibrillation control device 314 includes a catheter connection unit 40, a contact switching unit 42, a waveform output unit 44, a waveform input unit 46, a power source unit 48, an operation button 50, a control unit 352, a display unit 54, a speaker 56, a first transmission unit 320, and a first reception unit 322.

The control unit 352 includes a mode control unit 352*a*, the synchronization determination unit 352*e*, and a warning unit 252*d*. The control unit 352 is different from the third embodiment in that the synchronization determination unit 352*e* is provided instead of the trigger detection unit 52*b*.

The synchronization determination unit 352*e* determines whether a trigger signal received by the first reception unit 322 is synchronized with an electrocardiographic waveform input to the waveform input unit 46. For example, the synchronization determination unit 352*e* detects the peak position of an R wave of the electrocardiographic waveform by using the same method as the method of the trigger detection unit 52*b*, and determines whether the detection timing and the trigger signal are synchronized with each other. When the detection timing and the trigger signal are determined to be synchronized with each other, trigger points (for example, trigger markers 74*a* to 74*e* in FIG. 6) based on the trigger signal are displayed on the display unit 54.

In the discharge mode 72*c*, the mode control unit 352*a* supplies electrical energy to the electrode catheter 12 in synchronization with the trigger points based on the trigger signal received by the first reception unit 322.

When no trigger signal is transmitted to the first reception unit 322, the first transmission unit 320 transmits a trigger abnormal signal to the monitoring device 316. When the synchronization determination unit 352*e* determines that the trigger signal is not synchronized, the first transmission unit 320 transmits the trigger abnormal signal to the monitoring device 316. Similarly to the first transmission unit 220 according to the third embodiment, when the supplying of electrical energy is completed in the discharge mode 72*c*, the first transmission unit 320 transmits a supply completion signal to the monitoring device 316.

The first reception unit 322 receives a trigger signal indicating a trigger point from the monitoring device 316. Similarly to the first reception unit 222 according to the third embodiment, the first reception unit 322 receives an abnormal signal indicating detection of an earliest abnormal waveform or cardiac arrest from the monitoring device 316.

The monitoring device 216 includes a waveform acquisition unit 60, a waveform providing unit 62, a waveform selection unit 64, a second reception unit 324, a second transmission unit 326, an abnormality detection unit 232, the trigger detection unit 334, and a warning unit 330.

The second reception unit 324 receives the trigger abnormal signal from the defibrillation control device 314. Similarly to the second reception unit 224 according to the third embodiment, the second reception unit 324 receives the supply completion signal from the defibrillation control device 314.

The second transmission unit 326 transmits a trigger signal indicating a trigger point detected by the trigger detection unit 334 to the defibrillation control device 314. Similarly to the second transmission unit 226 according to the third embodiment, the second transmission unit 326 transmits, to the defibrillation control device 314, an abnormal signal indicating that the earliest abnormal waveform or cardiac arrest has been detected by the abnormality detection unit 232.

The trigger detection unit 334 detects a trigger point based on an electrocardiographic waveform being selected by the waveform selection unit 64, that is, an electrocardiographic waveform provided to the defibrillation control device 314 by the waveform providing unit 62.

The detection method of the trigger point by the trigger detection unit 334 may be the same method as the method of the trigger detection unit 52*b* according to the first embodiment or may be a method different from the method of the trigger detection unit 52*b*.

When no trigger point is detectable by the trigger detection unit 334, the warning unit 330 issues an alert. When the second reception unit 324 receives a trigger abnormal signal, the warning unit 330 issues an alert. When a predetermined operation for stopping the alert is performed, the warning unit 330 stops the alert by a warning display and a warning sound.

Figure 19:
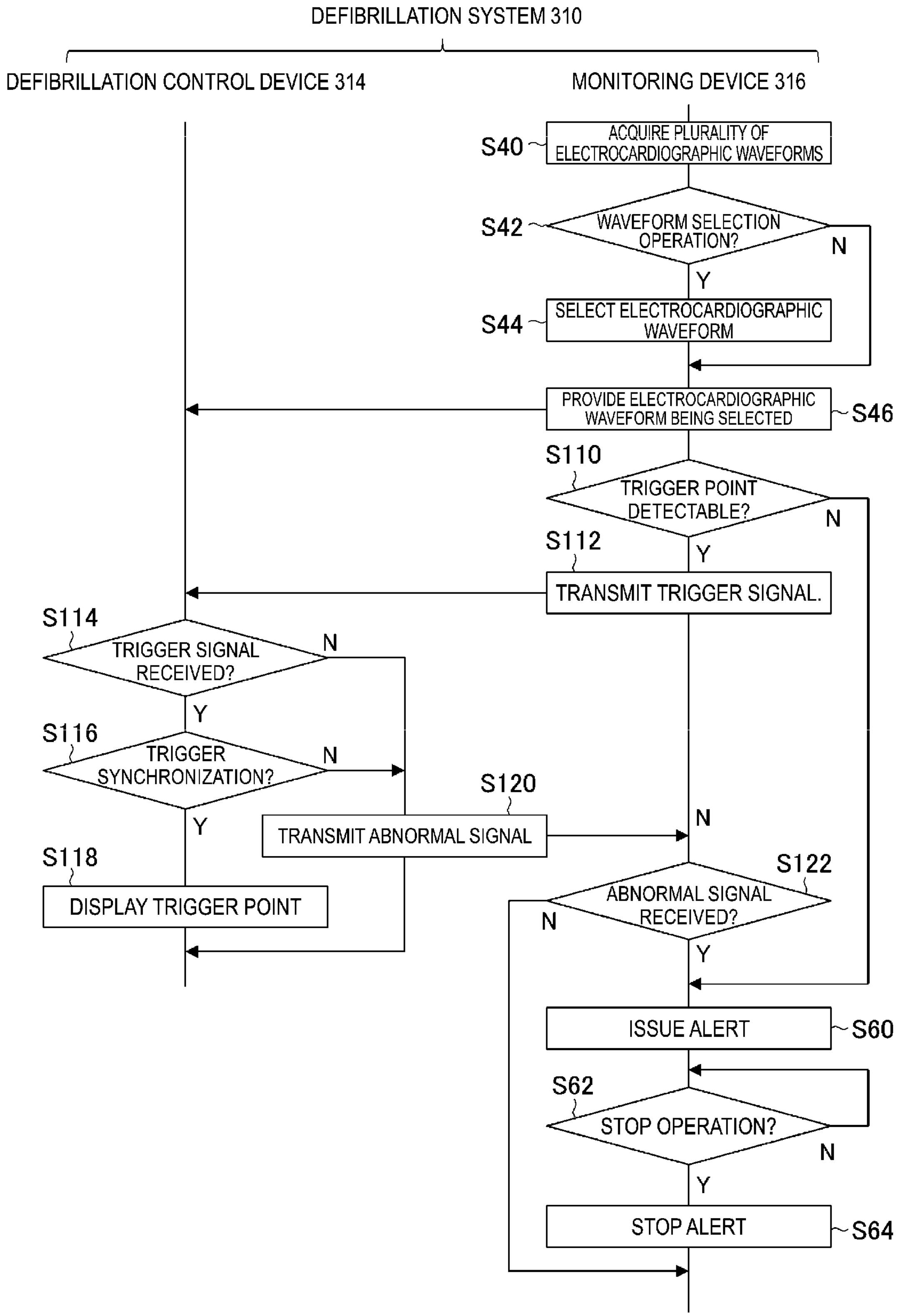
FIG. 19 is a flowchart schematically showing a trigger detection method according to the fourth embodiment.

FIG. 19 is a flowchart schematically illustrating a trigger detection method according to the fourth embodiment. In the flow of FIG. 19, the same processes as the processes in the flow of FIG. 14 are denoted by the same reference numerals.

The monitoring device 316 performs the same processes as the processes of steps S40, S42, S44, and S46 in FIG. 14. The trigger detection unit 334 detects a trigger point by using an electrocardiographic waveform being selected, and when the trigger point is detectable (Y in step S110), a trigger signal is transmitted from the second transmission unit 326 to the defibrillation control device 314 (step S112).

When the first reception unit 322 receives the trigger signal (Y in step S114) and the synchronization determination unit 352*e* determines that the trigger signal is synchronized (Y in step S116), the defibrillation control device 314 causes the display unit 54 to display trigger points (for example, trigger markers 74*a* to 74*e* in FIG. 6) (step S118). When the first reception unit 322 receives no trigger signal (N in step S114) or when the synchronization determination unit 352*e* determines that the trigger signal is not synchronized (N in step S116), the defibrillation control device 314 transmits a trigger abnormal signal from the first transmission unit 320 to the monitoring device 316 (step S120).

When the second reception unit 324 receives the trigger abnormal signal (Y in step S122), the monitoring device 316 performs the same processes as the processes of steps S60, S62, and S64 in FIG. 14. When no trigger point is detectable in step S110 (N in step S110), the monitoring device 316 performs the same processes as the processes of steps S60, S62, and S64.

In step S122, when no trigger abnormal signal is received in step S122 (N in step S122), the processes of steps S60, S62, and S64 are skipped.

According to the present embodiment, the monitoring device 316 can detect a trigger point, and the defibrillation control device 314 can determine whether a trigger signal is synchronized. When the monitoring device 316 is able to detect no trigger point, the monitoring device 316 can issue an alert. When the defibrillation control device 314 is able to receive no trigger signal or even when no trigger signal is determined to be synchronized, the monitoring device 316 can issue an alert. Since a user can perform an electrocardiographic waveform switching operation by the monitoring device 316 after an alert stop operation of the monitoring device 316, the user needs to operate only one device. Also in the present embodiment, convenience for the user who uses the defibrillation system 310 can be improved.

As a modified example of the fourth embodiment, instead of causing the monitoring device 316 to issue an alert, the waveform selection unit 64 may automatically switch an electrocardiographic waveform being selected to another electrocardiographic waveform, as in the modified example of the second embodiment. The monitoring device 316 may also perform the processes of S68, S70, S72, and S74 in FIG. 15 instead of the processes of S60, S62, and S64 in FIG. 19. In this case, the monitoring device 316 may also perform the processes of S40, S42, S44, S45, and S46 in FIG. 15 instead of the processes of S40, S42, S44, and S46 in FIG. 19.

As a modified example of the fourth embodiment, the abnormality detection unit 52*c* may also be provided in the control unit 352 of the defibrillation control device 314 instead of providing the abnormality detection unit 232 in the monitoring device 316. Similarly to the defibrillation control device 14 according to the first embodiment, the defibrillation control device 314 may also detect an earliest abnormal waveform or cardiac arrest after defibrillation and issue an alert.

The present disclosure has been described above based on the embodiments. It is obvious to those skilled in the art that various variations can be made to the combination of the components and processing operations in the exemplary embodiments and that such variations are included in the scope of the present disclosure.

Aspects of the present disclosure are as follows.

A first aspect is a defibrillation control device including a power source unit that supplies electrical energy to an electrode catheter, an abnormality detection unit that detects an earliest abnormal waveform by using a plurality of electrocardiographic waveforms measured by a plurality of electrodes of the electrode catheter after supplying the electrical energy, and a warning unit that issues an alert upon detecting the earliest abnormal waveform. According to this aspect, by detecting the earliest abnormal waveform and issuing an alert, useful information can be quickly provided to a user such as a doctor who performs catheter treatment.

A second aspect is the defibrillation control device according to the first aspect in which the abnormality detection unit detects, among the plurality of electrocardiographic waveforms, an earliest waveform having an earliest start timing at which an amplitude is equal to or greater than a first threshold value after the supplying of the electrical energy, and detects the earliest abnormal waveform by using the earliest waveform. According to this aspect, the earliest abnormal waveform can be appropriately detected by detecting the earliest waveform from among the plurality of electrocardiographic waveforms.

A third aspect is the defibrillation control device according to the second aspect in which the abnormality detection unit detects waveform portions in which the amplitude of the earliest waveform is equal to or greater than the first threshold value, and detects the earliest abnormal waveform when the number of the detected waveform portions from the start timing until a reference time elapses is equal to or greater than a predetermined number. According to this aspect, an abnormal waveform in with a larger number of waveform portions having significant peaks than a normal waveform can be appropriately detected.

A fourth aspect is the defibrillation control device according to the second or third aspect in which the abnormality detection unit detects downward waveform portions in which the amplitude of the earliest waveform is equal to or greater than the first threshold value, and detects the earliest abnormal waveform when the number of the detected waveform portions from the start timing until a reference time elapses is equal to or greater than a predetermined number. According to this aspect, an abnormal waveform having a larger number of downward waveform portions than a normal waveform can be appropriately detected.

A fifth aspect is the defibrillation control device according to any one of the second to fourth aspects in which the abnormality detection unit measures a continuous time of a flat portion in which the amplitude of the earliest waveform is equal to or greater than a second threshold value smaller than the first threshold value, and detects the earliest abnormal waveform when the continuous time of the flat portion measured from the start timing until a reference time elapses does not exceed a predetermined value. According to this aspect, an abnormal waveform having a longer time length of one waveform range than a normal waveform can be appropriately detected. In particular, even when a flat portion is included between adjacent waveform portions, when the flat portion is equal to or less than a predetermined value, the flat portion is regarded as being included in one waveform range, and an abnormal waveform can be appropriately detected.

A sixth aspect is the defibrillation control device according to any one of the second to fifth aspects in which, the abnormality detection unit detects the earliest abnormal waveform when an electrode from which the earliest waveform is acquired is not a predetermined electrode. According to this aspect, an abnormal waveform caused by abnormal excitation different from normal transmission of an electrical signal in a cardiac cavity can be appropriately detected.

A seventh aspect is the defibrillation control device according to any one of the first to sixth aspects in which the abnormality detection unit detects start timings at which amplitudes of the plurality of electrocardiographic waveforms are equal to or greater than a first threshold value after the supplying of the electrical energy, and detects the earliest abnormal waveform by using a detection order of the start timings of the plurality of electrocardiographic waveforms. According to this aspect, an abnormal waveform caused by abnormal excitation different from normal transmission of an electrical signal in a cardiac cavity can be appropriately detected.

An eighth aspect is the defibrillation control device according to any one of the first to seventh aspects in which a display unit is further provided to display information indicating which of the plurality of electrodes is an electrode from which the earliest abnormal waveform is acquired. According to this aspect, information relating to the position of an abnormal excitation site can be notified, thereby improving convenience for a user.

A ninth aspect is a monitoring device including a waveform acquisition unit that acquires an electrocardiographic waveform, a waveform providing unit that provides the electrocardiographic waveform to a defibrillation control device that supplies electrical energy to an electrode catheter, a reception unit that receives a trigger signal indicating a possible supply start timing of the electrical energy from the defibrillation control device, and a synchronization determination unit that determines whether the trigger signal is synchronized with the electrocardiographic waveform. According to this aspect, in the monitoring device that provides the electrocardiographic waveform to the defibrillation control device, whether a trigger point can be appropriately detected by the defibrillation control device can be determined. Thus, whether an appropriate electrocardiographic waveform can be provided to the defibrillation control device can be unitarily ascertained by the monitoring device, thereby improving convenience for a user.

A tenth aspect is the monitoring device according to the ninth aspect in which a warning unit is further provided to issue an alert when the trigger signal is determined not to be synchronized. According to this aspect, when no trigger point is appropriately detectable by the defibrillation control device, an alert is issued by the monitoring device. Therefore, after an alert stop operation is performed by the monitoring device, a switching operation of an electrocardiographic waveform to be provided to the defibrillation control device can be performed by the monitoring device as is. As a result, since the alert stop operation and the switching operation of the electrocardiographic waveform can be completed only by the monitoring device, convenience for a user can be improved.

An eleventh aspect is the monitoring device according to the ninth aspect in which a warning unit is further provided to issue an alert when the reception unit receives an abnormal signal from the defibrillation control device. According to this aspect, when the abnormal signal is received from the defibrillation control device, an alert is issued by the monitoring device. Therefore, after an alert stop operation is performed by the monitoring device, a switching operation of an electrocardiographic waveform to be provided to the defibrillation control device can be performed by the monitoring device as is. As a result, since the alert stop operation and the switching operation of the electrocardiographic waveform can be completed only by the monitoring device, convenience for a user can be improved.

A twelfth aspect is the monitoring device according to the ninth aspect in which the waveform acquisition unit acquires a plurality of electrocardiographic waveforms, a waveform selection unit is further provided to select one of the plurality of electrocardiographic waveforms, the waveform providing unit provides the electrocardiographic waveform selected by the waveform selection unit, and the waveform selection unit selects an electrocardiographic waveform different from an electrocardiographic waveform being selected from the plurality of electrocardiographic waveforms when the trigger signal is determined not to be synchronized. According to this aspect, when no trigger point is appropriately detectable by the defibrillation control device, an electrocardiographic waveform to be provided to the defibrillation control device can be automatically switched, thereby reducing the time and effort of a user.

A thirteenth aspect is the monitoring device according to the ninth aspect in which the waveform acquisition unit acquires a plurality of electrocardiographic waveforms, a waveform selection unit is further provided to select one of the plurality of electrocardiographic waveforms, the waveform providing unit provides the electrocardiographic waveform selected by the waveform selection unit, and the waveform selection unit selects an electrocardiographic waveform different from an electrocardiographic waveform being selected from the plurality of electrocardiographic waveforms when the reception unit receives an abnormal signal from the defibrillation control device. According to this aspect, when the abnormal signal is received from the defibrillation control device, an electrocardiographic waveform to be provided to the defibrillation control device can be automatically switched, thereby reducing the time and effort of a user.

A fourteenth aspect is the monitoring device according to any one of the ninth to thirteenth aspect in which a reception unit receives a supply completion signal of the electrical energy from the defibrillation control device, an abnormality detection unit detects an earliest abnormal waveform by using a plurality of electrocardiographic waveforms measured by a plurality of electrodes of the electrode catheter after the supply completion signal is received, and a transmission unit transmits an abnormal signal to the defibrillation control device upon detecting the earliest abnormal waveform. According to this aspect, by detecting the earliest abnormal waveform and transmitting the abnormal signal to the defibrillation control device, the defibrillation control device can issue an alert. Thus, useful information can be quickly provided to a user such as a doctor who performs catheter treatment.

A fifteenth aspect is a monitoring device including a reception unit that receives a supply completion signal of electrical energy from a defibrillation control device that supplies the electrical energy to an electrode catheter, a detection unit that detects an earliest abnormal waveform by using a plurality of electrocardiographic waveforms acquired by a plurality of electrodes of the electrode catheter after the supply completion signal is received, and a transmission unit that transmits an abnormal signal to the defibrillation control device upon detecting the earliest abnormal waveform. According to this aspect, by detecting the earliest abnormal waveform and transmitting the abnormal signal to the defibrillation control device, the defibrillation control device can issue an alert. Thus, useful information can be quickly provided to a user such as a doctor who performs catheter treatment.

A sixteenth aspect is a defibrillation control device including a power source unit that supplies electrical energy to an electrode catheter, a waveform input unit that receives an electrocardiographic waveform provided from a monitoring device, a reception unit that receives a trigger signal indicating a possible supply start timing of the electrical energy from the monitoring device, a synchronization determination unit that determines whether the trigger signal is synchronized with the electrocardiographic waveform, and a transmission unit that transmits an abnormal signal to the monitoring device when the trigger signal is not synchronized. According to this aspect, the defibrillation control device can determine whether a trigger point can be appropriately detected in the monitoring device that provides the electrocardiographic waveform and the trigger signal to the defibrillation control device, and can notify the monitoring device of an abnormality when the abnormality is present. Thus, the monitoring device can unitarily ascertain whether an appropriate electrocardiographic waveform and trigger signal can be provided to the defibrillation control device, thereby improving convenience for a user.

The configuration, operation, and function of each device and each method described above can be implemented by hardware resources or software resources, or by cooperation of the hardware resources and the software resources. As the hardware resources, various integrated circuits including, for example, a processor such as a central processing unit (CPU) and a memory such as a read only memory (ROM) and a random access memory (RAM) can be used. For example, programs such as operating systems and applications can be used as the software resources.

While preferred embodiments of the disclosure have been described above, it is to be understood that variations and modifications will be apparent to those skilled in the art without departing from the scope and spirit of the disclosure. The scope of the disclosure, therefore, is to be determined solely by the following claims.

The invention claimed is:

1. A defibrillation control device, comprising:

a power source unit that supplies electrical energy to an electrode catheter;

a processor; and a memory storing instructions that, when executed by the processor, cause the processor to perform operations comprising:

detecting an earliest abnormal waveform on a millisecond timescale by using a plurality of electrocardiographic waveforms measured by a plurality of electrodes of the electrode catheter after supplying the electrical energy; and issuing an alert upon detecting the earliest abnormal waveform, wherein the detecting the earliest abnormal waveform comprises:

detecting an earliest waveform having an earliest start timing at which an amplitude is equal to or greater than a first threshold value after the supplying of the electrical energy, among the plurality of electrocardiographic waveforms;

detecting start timings at which amplitudes of the plurality of electrocardiographic waveforms are equal to or greater than the first threshold value after the supplying of the electrical energy:

determining whether the earliest waveform is normal or abnormal by using a detection order of the start timings of the plurality of electrocardiographic waveforms Including the earliest waveform; and detecting the earliest abnormal waveform when the earliest waveform is determined to be abnormal.

2. The defibrillation control device according to claim 1, wherein the operations performed by the processor further comprises detecting waveform portions in which the amplitude of the earliest waveform is equal to or greater than the first threshold value, and wherein the earliest abnormal waveform is detected when the number of the detected waveform portions from the start timing until a reference time elapses is equal to or greater than a predetermined number.

3. The defibrillation control device according to claim 1, wherein the operations performed by the processor further comprises detecting downward waveform portions in which the amplitude of the earliest waveform is equal to or greater than the first threshold value, and wherein the earliest abnormal waveform is detected when the number of the detected waveform portions from the start timing until a reference time elapses is equal to or greater than a predetermined number.

4. The defibrillation control device according to claim 1, wherein the operations performed by the processor further comprises measuring a continuous time of a flat portion in which the amplitude of the earliest waveform is equal to or greater than a second threshold value smaller than the first threshold value, and wherein the earliest abnormal waveform is detected when the continuous time of the flat portion measured from the start timing until a reference time elapses does not exceed a predetermined value.

5. The defibrillation control device according to claim 1, wherein the earliest abnormal waveform is detected when an electrode from which the earliest waveform is acquired is not a predetermined electrode.

6. The defibrillation control device according to claim 1, further comprising:

a display unit that displays information indicating which of the plurality of electrodes is an electrode from which the earliest abnormal waveform is acquired.

7. The defibrillation control device according to claim 1, wherein the operations performed by the processor further comprises ending the detecting the earliest abnormal waveform when the earliest abnormal waveform is detected or when neither the earliest abnormal waveform nor cardiac arrest is detected within 10 seconds after the completion of the supply of electrical energy.

8. A defibrillation control device comprising:

a power source unit that supplies electrical energy to an electrode catheter;

a processor; and a memory storing instructions that, when executed by the processor, cause the processor to perform operations comprising:

detecting an earliest abnormal waveform on a millisecond timescale by using a plurality of electrocardiographic waveforms measured by a plurality of electrodes of the electrode catheter after supplying the electrical energy;

ending the detecting the earliest abnormal waveform when the earliest abnormal waveform is detected or when neither the earliest abnormal waveform nor cardiac arrest is detected within 10 seconds after the completion of the supply of electrical energy; and issuing an alert upon detecting the earliest abnormal waveform, wherein the detecting the earliest abnormal waveform comprises:

detecting start timings at which amplitudes of the plurality of electrocardiographic waveforms are equal to or greater than a first threshold value after the supplying of the electrical energy, and wherein the earliest abnormal waveform is detected by using a detection order of the start timings of the plurality of electrocardiograms.

* * * * *